United States Patent
Gaweco et al.

(10) Patent No.: US 9,050,334 B2
(45) Date of Patent: *Jun. 9, 2015

(54) MIF INHIBITORS AND THEIR USES

(75) Inventors: Anderson Gaweco, Brooklyn, NY (US); John K. Walker, St. Charles, MO (US); Joseph B. Monahan, St. Louis, MO (US); Jerry W. Cubbage, Wildwood, MO (US); Jeffery Carroll, St. Louis, MO (US)

(73) Assignee: INNOV88 LLC, Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/184,058

(22) Filed: Jul. 15, 2011

(65) Prior Publication Data

US 2012/0035150 A1 Feb. 9, 2012

Related U.S. Application Data

(60) Provisional application No. 61/365,070, filed on Jul. 16, 2010, provisional application No. 61/381,662, filed on Sep. 10, 2010.

(51) Int. Cl.

| | | |
|---|---|---|
| *C07D 215/38* | (2006.01) | |
| *A61K 31/47* | (2006.01) | |
| *C07D 215/54* | (2006.01) | |
| *C07D 401/12* | (2006.01) | |
| *C07D 401/14* | (2006.01) | |
| *C07D 409/14* | (2006.01) | |
| *C07D 417/14* | (2006.01) | |

(52) U.S. Cl.
CPC .............. *A61K 31/47* (2013.01); *C07D 215/54* (2013.01); *C07D 401/12* (2013.01); *C07D 401/14* (2013.01); *C07D 409/14* (2013.01); *C07D 417/14* (2013.01)

(58) Field of Classification Search
CPC ............................ A01B 12/006; C07D 401/14
USPC ........................................... 546/159; 514/312
See application file for complete search history.

(56) References Cited

U.S. PATENT DOCUMENTS

| | | | | |
|---|---|---|---|---|
| 6,921,821 | B2 * | 7/2005 | Blackburn et al. ............ | 540/364 |
| 7,060,697 | B2 | 6/2006 | Marsilje et al. | |
| 7,173,036 | B2 * | 2/2007 | Sircar et al. .............. | 514/253.07 |
| 7,235,546 | B2 * | 6/2007 | Sircar et al. .................. | 514/218 |
| 7,312,220 | B2 * | 12/2007 | Sircar et al. .............. | 514/253.07 |
| 7,312,221 | B2 * | 12/2007 | Sircar et al. .............. | 514/253.07 |
| 7,432,374 | B2 | 10/2008 | Gaeta et al. | |

FOREIGN PATENT DOCUMENTS

| | | |
|---|---|---|
| WO | WO2004/074218 | 9/2004 |
| WO | WO2005/021546 | 3/2005 |
| WO | WO2008/152149 | 12/2008 |

OTHER PUBLICATIONS

Mekheimer, Bull Chem Soc Jpn, 66, 2936-2940, 1993.*
Mekheimer, CA 129:216502, abstract only of Het Comm, vol. 4(2), pp. 131-138, 1998.*
Mekheimer, CA 151:221083, abstract only of J Chem Res, vol. 12, pp. 735-737, 2008.*
McLean, Bioorg & Med Chem Letters, vol. 20, p. 1821-1824, 2010.*
U.S. Appl. No. 14/237,136, filed Apr. 2011, Gaweco.*
Mekheimer et al., A Novel Nucleophilip Substitution with Quinoline Derivatives. Synthesis of Quinolones and Pyrazolo[4,3-c] quinoline Derivatives, Bull Chem Soc Jpn, 66, pp. 2936-2940, 1993.
Mekheimer et al., Nucleophilic substitution of 2,4-dichloroquinoline-3-carbonitrile with different nucleophiles. Synthesis of several new quinoline-3-carbonitrile derivatives, 129:216502, abstract only of Het Comm, vol. 4(2), pp. 131-138, 1998 (abstract).
Mekheimer et al., Fused quinoline heterocycles VIII. Synthesis of polyfunctionally substituted pyrazolo[4, 3-c]quinolin-4(5H)-ones, J. Chem. Research, 151:221083, vol. 12, pp. 735-737, 2008 (abstract).
Cournia et al., Discovery of Human Macrophage Migration Inhibitory Factor (MIF)-CD74, Antagonists via Virtual Screening, J Med Chem., vol. 52(2): 416-424; pp. 2-4, 2009 (abstract).

* cited by examiner

*Primary Examiner* — D M Seaman

(57) ABSTRACT

The invention relates to MIF inhibitors; compositions comprising an effective amount of a MIF inhibitor; and methods for treating or preventing diseases associated with MIF.

12 Claims, No Drawings

MIF INHIBITORS AND THEIR USES

PRIORITY

The application claims the benefit of U.S. Provisional Application No. 61/365,070 filed Jul. 16, 2010 and U.S. Provisional Application No. 61/381,662 filed Sep. 10, 2010, the entire disclosures of these applications are relied on for all purposes and incorporated into this application by reference.

GOVERNMENT SUPPORT

Research leading to this invention was in part funded by the NIH Grant Number 1R43AI096570-01 from the National Institute of Allergy and Infectious Diseases.

FIELD OF THE INVENTION

The invention relates to Macrophage Migration Inhibitory Factor (MIF) associated diseases and disorders. More particularly, the invention relates to MIF inhibitors; compositions comprising an effective amount of a MIF inhibitor; and methods for treating or preventing MIF associated diseases and disorders.

BACKGROUND OF THE INVENTION

There are high unmet medical needs in the few established therapies for several cardiovascular and cerebrovascular diseases, autoimmune diseases and inflammatory disorders, fibrotic diseases, metabolic diseases and oncologic diseases. Despite the diverse clinical manifestations of these diseases, they share a unique common disease pathogenesis characterized by organ and tissue damage arising from dysregulated immune responses and production of critical inflammatory mediators. Only recently has the overlapping mechanistic role of MIF been well-characterized and target validated in several animal models of some of these diseases.

MIF is a pro-inflammatory cytokine secreted by activated T cells and macrophages that critically regulates inflammation. MIF plays an important role in the host innate and adaptive immune responses through its direct biological function and also through downstream signaling events following its binding with its known receptors CD74, CXCR2 and CXCR4 (Greven et al., 2010; Morand et al., 2006; Calandra and Roger, 2003; Gore et al., 2008; Bernhagen et al., 2007; Cho et al., 2010; McLean et al., 2010; Weber et al., 2008). MIF is an important mediator in the initiation and perpetuation of the inflammatory process through T-cell proliferation, B-cell antibody production, macrophage activation and induction of inflammatory mediators, as well as cell growth promotion, angiogenesis and counter-regulation of glucocorticoids contributing to disease progression. MIF has been implicated in the pathogenesis of a wide range of disorders including cardiovascular and cerebrovascular diseases, autoimmune and inflammatory diseases, fibrotic diseases, metabolic diseases, and oncologic diseases. Thus, MIF is a therapeutic target for many diseases and disorders.

Among cytokines, MIF is unique because it functions as an enzyme exhibiting tautomerase catalytic activity which was initially thought to underlie MIF's biologic function. The tautomerase enzyme catalytic activity site is located within the canonical deep pocket of MIF. As such, most first generation MIF inhibitors selectively target this MIF catalytic activity site. It has recently been demonstrated that inhibition of MIF tautomerase activity is not tantamount to complete inhibition of MIF biological properties (Fingerle-Rowson et al., 2009). In particular, a tautomerase-null, Pro->Gly1 MIF protein (P1G-MIF) knock-in mouse model showed in this study that intrinsic tautomerase enzyme activity is dispensable for MIF's biological properties. Catalytically inactive P1G-MIF shows preservation, albeit attenuated, of MIF biological functions and of CD74- and CXCR2-binding, supporting the important role for other specific residues and motifs in MIF within and outside the catalytic site that regulates function and receptor interactions.

Recent advances in the structural biology and chemistry of MIF have revealed critical pharmacophores in addition to those in the MIF tautomerase catalytic site that should serve as important targets for the development of MIF inhibitors which display better target binding specificity and enhanced therapeutic efficacy against MIF-related diseases (Greven et al., 2010; Morand et al., 2006; Calandra and Roger, 2003; Gore et al., 2008; Bernhagen et al., 2007; Cho et al., 2010; McLean et al., 2010). For example, a new allosteric surface binding pocket has been discovered at the mouth of the canonical deep pocket catalytic site that contains specific residues important for MIF conformational changes and receptor binding (McLean et al., 2010; Cho et al., 2010). These specific MIF residues within the canonical deep pocket and the surface allosteric binding site of MIF have been identified to be important contact sites for CD74 and CXCR2 receptor binding which mediate critical MIF signal transduction activity.

Recent advances in understanding the complex biology of MIF have demonstrated MIF functioning not only through interaction with CD74, but also through CXCR2 and CXCR4 receptors (Bernhagen et al., 2007; Weber et al., 2008). Furthermore, specific residues on MIF have been described as critical for interaction with CD74, CXCR2, and CXCR4 receptors and these have not been concomitantly targeted by first generation MIF tautomerase inhibitors (Cournia et al., 2009; Weber et al., 2008; McLean et al., 2010). Lack of inhibition by these first generation MIF inhibitors of MIF/receptor binding and thus numerous MIF-induced downstream signal transduction events have limited their therapeutic potential in MIF-related diseases. Most of the first generation MIF inhibitors do not reflect the scientific developments on MIF biology and chemistry which have recently emerged. These first generation MIF inhibitors mostly targeted the MIF enzymatic tautomerase activity located at the canonical deep pocket site around the N-terminal Pro-1 region and do not target either the surface allosteric site or the specific MIF residues within both binding sites critical for receptor interactions. Such a catalytic site-specific approach utilized by the first generation MIF inhibitors may be the reason that certain MIF biological functions and MIF-mediated signal transduction events remain partially uninhibited in the presence of these inhibitors due to insufficient conformational change of MIF and incomplete inhibition of MIF:receptor binding. In contrast, inhibitors which interact with a combination of allosteric and catalytic sites will induce a conformational change and block both tautomerase activity and critical MIF:receptor interactions resulting in effective functional antagonism and blockade of downstream signaling.

Thus, new inhibitors of MIF are currently needed for use in treating MIF associated diseases and disorders.

SUMMARY OF THE INVENTION

The invention is based in part on the discovery of MIF inhibitors which interact with multiple binding sites on MIF and thereby inhibit interaction of MIF with its biological targets. The invention is also based on compositions comprising an effective amount of a MIF inhibitor; and methods for treating or preventing disorders associated with high MIF expression and or activity, comprising the administration of an effective amount of a MIF inhibitor.

In one aspect, compounds are described which inhibit the binding of MIF to CD74, CXCR2, and/or CXCR4 receptors. These compounds comprise two regions, A and B, linked by a chemical tether, with the A region binding to the allosteric surface binding pocket site and the B region binding to the canonical deep pocket tautomerase catalytic site. The A region interacts with Tyr36, Trp108, Phe113, and/or other residues of MIF. Thus, A is a substituent capable of pi stacking with Tyr36 causing a rotational displacement of this residue which is critical for effective receptor binding. The B region interacts with a combination of Pro 1, Tyr95, Ile64 and/or other residues in the MIF catalytic site through hydrophobic interactions and hydrogen bonding. The tether between the A and B regions of the compound must be of appropriate length and flexibility to allow optimal association with the residues mentioned above while at the same time being rigid enough to maintain conformational integrity needed for initial interaction with the two receptor binding sites. Furthermore, the tether is able to form a hydrophobic interaction with Asn97 in the catalytic pocket.

In another aspect, compounds of the Formula I are described:

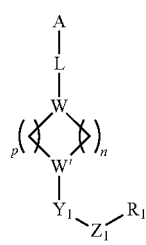

I and pharmaceutically acceptable salts, hydrates, solvates, prodrugs, and tautomers thereof;
wherein
A is an monocyclic or bicyclic aryl or a monocyclic or bicyclic heteroaryl;
L is a bond, —$CH_2$—, —$NR_2$—, S, or O;
each n and p is independently 1, 2, or 3;
each W and W' is independently N or CH, provided that when L is a bond and p and n are each 2 then W and W' can not simultaneously both be N;
$Y_1$ is null, a bond, —C(O)—, —$CH_2$—, —$NR_2$—, $SO_2$, S(O), or O;
$Z_1$ is a bond, O, S, $CH_2$, —C(O)—, —C(O)N($R_3$)(R4), —N(R3)(R4), —SO2—, or —$SO_2$N($R_3$)(R4);
$R_1$ is null, a substituted straight chain or branched $C_1$-$C_6$ alkyl, a straight chain or branched $C_2$-$C_6$ alkene, a straight chain or branched $C_2$-$C_6$ alkyne, a $C_3$-$C_4$ cyclic alkyl, aromatic or nonaromatic monocyclic carbocycle, or aromatic or nonaromatic monocyclic heterocycle, wherein $R_1$ is optionally substituted;
$R_2$ is H, —$C_1$-$C_6$ alkyl, —$C_2$-$C_6$ alkene, —C(O)($C_1$-$C_6$alkyl), —C(O)NH($C_1$-$C_6$alkyl), ($C_0$-$C_3$)—($C_3$-$C_6$)cycloalkyl, or benzyl, wherein $R_2$ is optionally substituted;
$R_3$ and $R_4$ are each independently null, H, —$C_1$-$C_6$ alkyl, —($C_1$-$C_6$alkyl)aryl, aryl, —$C_3$-$C_6$(cycloalkyl); or $R_3$ and $R_4$, when taken together with the nitrogen to which they are attached, can form a heterocycle containing from one to three heteroatoms selected from N, O, and S, and wherein $R_3$ and $R_4$ are optionally substituted.

In some embodiments, A is selected from indolyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, dihydropurinonyl, pyrrolopyrimidinyl, purinyl, pyrazolopyridinyl, pyrazolopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, quinolonyl, isoquinolonyl, phthalazinyl, benzodioxyl, indolinyl, benzisobiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, benzoxazepinyl, phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyridinyl, pyrimidinyl, pyrazinyl, pyridazinyl, and triazinyl. In some embodiments, A can be optionally substituted.

In other embodiments, A is selected from the group consisting of

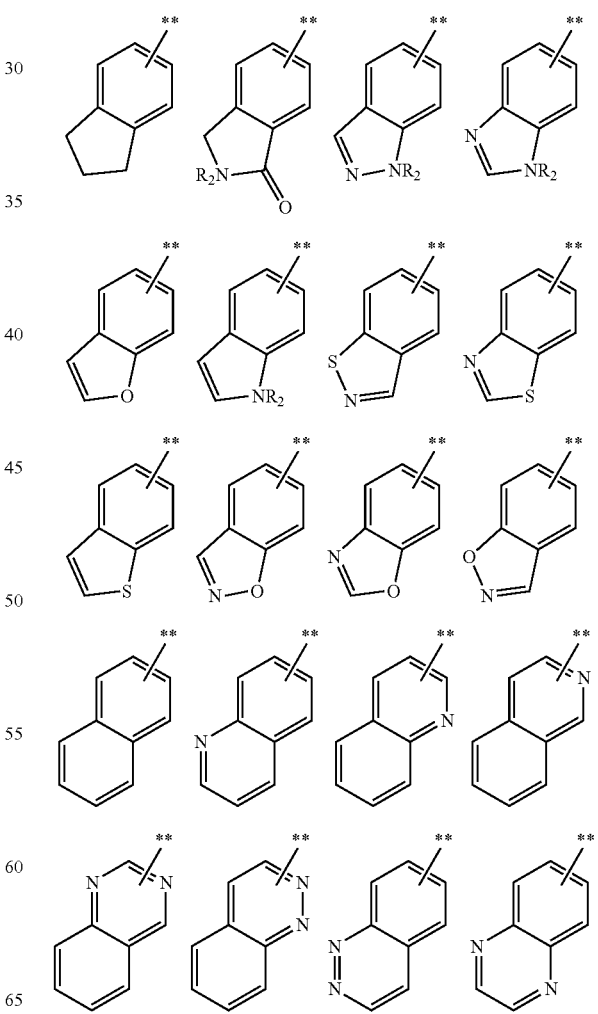

-continued

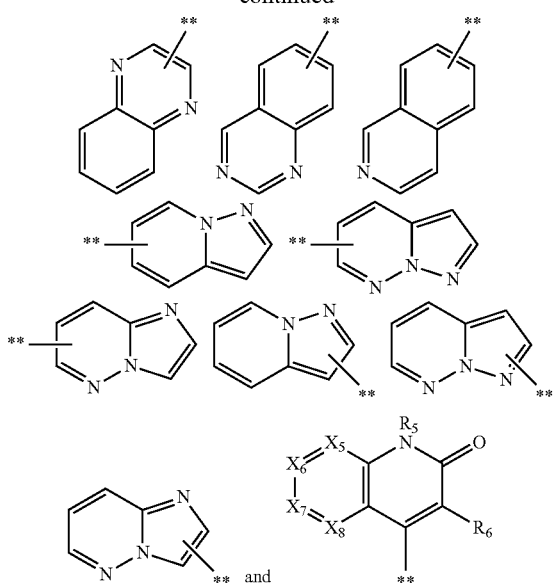

wherein
** is the site of attachment to L;
each of $X_5$, $X_6$, $X_7$, and $X_8$ is independently CH or N;
$R_5$ is H, —C1-C6 alkyl, —C2-C6 alkene, —(C0-C3 alkyl)-(C3-C6 cycloalkyl), —C(O)C1-C6alkyl, —C(O)NH(C1-C6alkyl), or benzyl; and wherein $R_5$ is optionally substituted;
$R_6$ is an electron withdrawing group; and
A is optionally substituted.

In still other embodiments, A is selected from the group consisting of

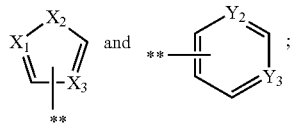

and
wherein
each of $X_1$ and $X_3$ is independently O, S, or N;
$X_2$ is $CH_2$, O, S, S=O, $SO_2$ or $NR_2$;
each of $Y_2$ and $Y_3$ is independently CH or N; and
A is optionally substituted.

In some embodiments, $R_1$ is selected from the group consisting of straight chain or branched C1-C6 alkyl, straight chain or branched C2-C6 alkene, straight chain or branched C2-C6 alkyne;

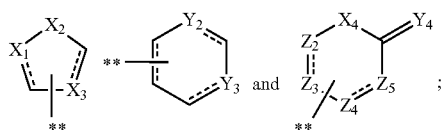

wherein
each ------ represents a single or double bond;
each of $X_1$ and $X_3$ is independently CH, O, S, or $NR_2$, provided that when $X_1$ or $X_3$ are attached to a single bond, then each of $X_1$ and $X_3$ is independently $CH_2$, O, S, or $NR_2$;
$X_2$ is $CH_2$, O, S, or $NR_2$;
$X_4$ is $NR_2$, $CH_2$, or O;
each of $Y_2$ and $Y_3$ is CH or N; provided that when $Y_2$ or $Y_3$ are attached to a single bond, then each of $Y_2$ and $Y_3$ is independently $CH_2$, or $NR_2$;
$Y_4$ is O or S;
each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently $CH_2$, or $NR_2$;
and
$R_1$ is optionally substituted.

In certain embodiments, A is

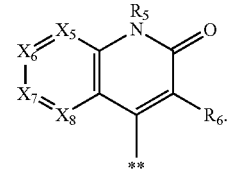

In a particular embodiment, each of $X_5$, $X_6$, $X_7$, and $X_8$ is CH, and $R_6$ is selected from —CN, —$NO_2$, —$CO_2H$, C(O)—Rx, —$CO_2$Rx, and —$CO_2$NRxRy, wherein Rx and Ry are each independently —$C_1$-$C_6$ alkyl, and wherein Rx and Ry, when taken together with the nitrogen to which they are attached, form a heterocycle containing from one to three heteroatoms selected from N, O, and S.

In other embodiments, $R_1$ is

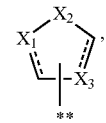

$X_1$ and $X_3$ are each CH; and
each ------ represents a double bond.
In some embodiments, $R_1$ is

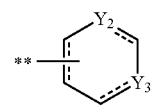

and $Y_3$ is CH and
each ------ represents a double bond.
In some embodiments, n is 2 and p is 2.
In some embodiments, W is N and W' is CH.
In some embodiments, n is 1 and p is 1.
In some embodiments, W is CH and W' is N.
In some embodiments, W and W' are each CH.
In some embodiments, $Y_1$ is a bond and Z is —C(O)—.
In some embodiments, L is a bond.
In some embodiments, L is $NR_2$ and $R_2$ is selected from —$C_1$-$C_6$alkyl, benzyl, and —($C_0$-$C_3$)—($C_3$-$C_6$ cycloalkyl), and $R_2$ is optionally substituted.
In some embodiments, $R_2$ is -cyclopropylmethyl, -benzyl or —$CH_2CH_2OH$.
In some embodiments, $R_2$ is selected from H or methyl.
In some embodiments, $R_6$ is —CN.
In some embodiments, $R_5$ is $C_1$-$C_6$ alkyl.

In some embodiments, $R_5$ is $CH_3$.
In some embodiments, $R_5$ is benzyl.
In another aspect, compounds of Formula II are described:

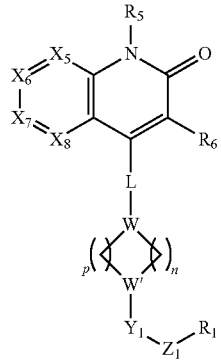

II and pharmaceutically acceptable salts, hydrates, solvates, prodrugs, and tautomers thereof;
wherein
each of $X_5$, $X_6$, $X_7$, and $X_8$ is independently CH or N;
L is a bond, —$CH_2$—, —$NR_2$—, S, or O;
each n and p is independently 1, 2, or 3;
each W and W' is independently N or CH, provided that when L is a bond and p and n are each 2 then W and W' can not simultaneously both be N;
$Y_1$ is null, a bond, —C(O)—, —$CH_2$—, —$NR_2$—, SO, $S(O)_2$ or O;
$Z_1$ is a bond, O, S, $CH_2$, —C(O)—, —C(O)N($R_3$)(R4), —N($R_3$)(R4), —$SO_2$—, or —$SO_2$N($R_3$)(R4);
$R_1$ is null, a straight chain or branched $C_1$-$C_6$ alkyl, a straight chain or branched $C_2$-$C_6$ alkene, a straight chain or branched $C_2$-$C_6$ alkyne, a $C_3$-$C_4$ cyclic alkyl, an aromatic or nonaromatic monocyclic carbocyle, or aromatic or nonaromatic monocyclic heterocycle, wherein $R_1$ is optionally substituted;
$R_2$ and $R_5$ are each independently H, —C1-C6 alkyl, —C2-C6 alkene, —(C0-C3 alkyl)-(C3-C6 cycloalkyl), —C(O)C1-C6alkyl, —C(O)NH(C1-C6alkyl), or benzyl; and wherein $R_2$ and $R_5$ are each independently optionally substituted;
$R_3$ and $R_4$ are each independently null, H, —$C_1$-$C_6$ alkyl, —($C_0$-$C_6$alkyl)aryl, —$C_3$-$C_6$(cycloalkyl); or $R_3$ and $R_4$, when taken together with the nitrogen to which they are attached, can form a heterocycle containing from one to three heteroatoms selected from N, O, and S, and wherein $R_3$ and $R_4$ are optionally substituted; and
$R_6$ is an electron withdrawing group.
In some embodiments, $R_1$ is selected from the group consisting of straight chain or branched $C_1$-$C_6$ alkyl, straight chain or branched C2-C6 alkene,

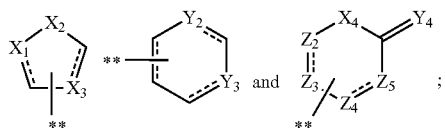

wherein
each ------ represents a single or double bond;
each of $X_1$ and $X_3$ is independently CH, O, S, or $NR_2$, provided that when $X_1$ or $X_3$ are attached to a single bond, then each of $X_1$ and $X_3$ is independently $CH_2$, O, S, or $NR_2$,
$X_2$ is $CH_2$, O, S, or $NR_2$,
$X_4$ is $NR_2$, $CH_2$, or O;
each of $Y_2$ and $Y_3$ is CH or N; provided that when $Y_2$ or $Y_3$ are attached to a single bond, then each of $Y_2$ and $Y_3$ is independently $CH_2$, or $NR_2$;
$Y_4$ is O or S;
each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently $CH_2$, or $NR_2$;
and
$R_1$ is optionally substituted.
In some embodiments, $R_1$ is

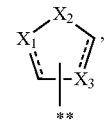

$X_1$ and $X_3$ are each CH; and
each ------ represents a double bond.
In some embodiments, $R_1$ is

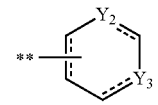

and $Y_3$ is CH and
each ------ represents a double bond.
In some embodiments, $R_6$ is selected from the group consisting of —CN, —$NO_2$, —$CO_2$H, C(O)—Rx, —CO2Rx, and —$CO_2$NRxRy, wherein Rx and Ry are each independently —$C_1$-$C_6$ alkyl, and wherein Rx and Ry, when taken together with the nitrogen to which they are attached, form a heterocycle containing from one to three heteroatoms selected from N, O, and S.
In some embodiments, p is 2 and n is 2.
In some embodiments, p is 1 and n is 1.
In some embodiments, n is 3.
In some embodiments, L is a bond or $NR_2$ and $R_2$ is H or $CH_3$.
In another aspect, compounds of Formula IIa are described:

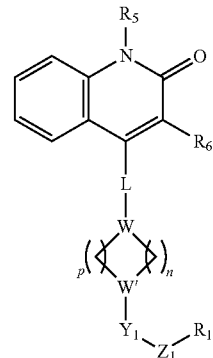

IIa and pharmaceutically acceptable salts, hydrates, solvates, prodrugs, and tautomers thereof;
wherein
L is a bond, —CH$_2$—, —NR$_2$—, S, or O;
each n and p is independently 1, 2, or 3;
each W and W' is independently N or CH, provided that when L is a bond and p and n are each 2 then W and W' can not simultaneously both be N;
Y$_1$ is null, a bond, —C(O)—, —CH$_2$—, —NR$_2$—, or O;
Z$_1$ is a bond, O, S, CH$_2$, —C(O)—, —C(O)N(R$_3$)(R4), —N(R3)(R4), —SO2—, or —SO$_2$N(R$_3$)(R4);
R$_1$ is null, a straight chain or branched C$_1$-C$_6$ alkyl, a straight chain or branched C$_2$-C$_6$ alkene, a straight chain or branched C$_2$-C$_6$ alkyne, a C$_3$-C$_4$ cyclic alkyl, an aromatic or nonaromatic monocyclic carbocycle, or aromatic or nonaromatic monocyclic heterocycle, wherein R$_1$ is optionally substituted;
R$_2$ and R$_5$ are each independently H, —C2-C6 alkyl, —C2-C6 alkene, —(C0-C3 alkyl)-(C3-C6 cycloalkyl), —C(O)C1-C6alkyl, —C(O)NH(C1-C6alkyl), or benzyl; and wherein R$_2$ and R$_5$ are each independently optionally substituted;
R$_3$ and R$_4$ are each independently null, H, —C$_1$-C$_6$ alkyl, —(C$_1$-C$_6$alkyl)aryl, aryl, —C$_3$-C$_6$(cycloalkyl); or R$_3$ and R$_4$, when taken together with the nitrogen to which they are attached, can form a heterocycle containing from one to three heteroatoms selected from N, O, and S, and wherein R$_3$ and R$_4$ are optionally substituted; and
R$_6$ is an electron withdrawing group.
In some embodiments, R$_1$ is selected from the group consisting of a straight chain or branched C1-C6 alkyl, a straight chain or branched C2-C6 alkene,

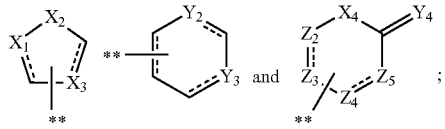

wherein
each ------ represents a single or double bond;
each of X$_1$ and X$_3$ is independently CH, O, S, or NR$_2$, provided that when X$_1$ or X$_3$ are attached to a single bond, then each of X$_1$ and X$_3$ is independently CH$_2$, O, S, or NR$_2$;
X$_2$ is CH$_2$, O, S, or NR$_2$,
X$_4$ is NR$_2$, CH$_2$, or O;
each of Y$_2$ and Y$_3$ is CH or N; provided that when Y$_2$ or Y$_3$ are attached to a single bond, then each of Y$_2$ and Y$_3$ is independently CH$_2$, or NR$_2$;
Y$_4$ is O or S;
each of Z$_2$, Z$_3$, Z$_4$, and Z$_5$ is independently N or CH; provided that when Z$_2$, Z$_3$, Z$_4$, and Z$_5$ are attached to a single bond, then each of Z$_2$, Z$_3$, Z$_4$, and Z$_5$ is independently CH$_2$, or NR$_2$;
and
R$_1$ is optionally substituted.
In some embodiments, R$_1$ is

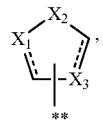

X$_1$ and X$_3$ are each CH; and
each ------ represents a double bond.
In some embodiments, R$_1$ is

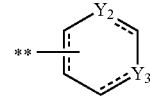

and Y$_3$ is CH and
each ------ represents a double bond.
In some embodiments, R$_6$ is selected from the group consisting of —CN, —NO$_2$, —CO$_2$H, C(O)—Rx, —CO$_2$Rx, and —CO$_2$NRxRy, wherein Rx and Ry are each independently —C$_1$-C$_6$ alkyl, and wherein Rx and Ry, when taken together with the nitrogen to which they are attached, form a heterocycle containing from one to three heteroatoms selected from N, O, and S.
In some embodiments, p is 2 and n is 2.
In some embodiments, p is 1 and n is 1.
In some embodiments, n is 3.
In some embodiments, L is a bond or NR$_2$ and R$_2$ is H or CH$_3$.
In another aspect, compounds of Formula III are described:

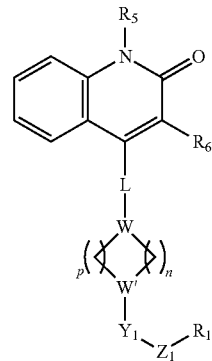

III and pharmaceutically acceptable salts, hydrates, solvates, prodrugs, and tautomers thereof;
wherein
L is a bond, —CH$_2$—, —NR$_2$—, S, or O;
each n and p is independently 1, 2, or 3;
each W and W' is independently N or CH, provided that when L is a bond and p and n are each 2 then W and W' can not simultaneously both be N;
Y$_1$ is null, a bond, SO, S(O)$_2$, —C(O)—, —CH$_2$—, —NR$_2$—, or O;
Z$_1$ is a bond, S, O, —C(O)—, —C(O)N(R$_3$)(R4), —N(R3)(R4), —SO2—, SO, or —SO$_2$N(R$_3$)(R4);
R$_1$ is selected from the group consisting of null, a straight chain or branched C1-C6 alkyl, a straight chain or branched C2-C6 alkene,

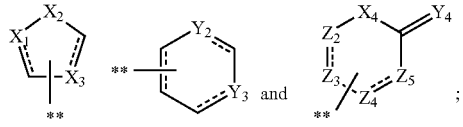

wherein each ------ represents a single or double bond;

each of $X_1$ and $X_3$ is independently CH, O, S, or $NR_2$, provided that when $X_1$ or $X_3$ are attached to a single bond, then each of $X_1$ and $X_3$ is independently $CH_2$, O, S, or $NR_2$, $X_2$ is $CH_2$, O, S, or $NR_2$;

$X_4$ is $NR_2$, $CH_2$, or O;

each of $Y_2$ and $Y_3$ is CH or N; provided that when $Y_2$ or $Y_3$ are attached to a single bond, then each of $Y_2$ and $Y_3$ is independently $CH_2$, or $NR_2$, $Y_4$ is O or S;

each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently $CH_2$, or $NR_2$;

and $R_1$ is optionally substituted;

$R_2$ and $R_5$ are each independently H, —C1-C6 alkyl, —C2-C6 alkene, —(C0-C3 alkyl)-(C3-C6 cycloalkyl), —C(O)C1-C6alkyl, —C(O)NH(C1-C6alkyl), or benzyl; and wherein $R_2$ and $R_5$ are each independently optionally substituted;

$R_3$ and $R_4$ are each independently null, H, —$C_1$-$C_6$ alkyl, —($C_1$-$C_6$alkyl)aryl, aryl, —$C_3$-$C_6$(cycloalkyl); or $R_3$ and $R_4$, when taken together with the nitrogen to which they are attached, can form a heterocycle containing from one to three heteroatoms selected from N, O, and S, and wherein $R_3$ and $R_4$ are optionally substituted; and $R_6$ is an electron withdrawing group.

In some embodiments, $R_1$ is

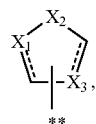

$X_1$ and $X_3$ are each CH; and each ------ represents a double bond.

In some embodiments, $R_1$ is

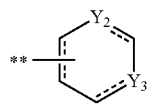

and $Y_3$ is CH and each ------ represents a double bond.

In some embodiments, $R_6$ is selected from the group consisting of —CN, —$NO_2$, —$CO_2H$, C(O)—Rx, —$CO_2Rx$, and —$CO_2NRxRy$, wherein Rx and Ry are each independently —$C_1$-$C_6$ alkyl, and wherein Rx and Ry, when taken together with the nitrogen to which they are attached, form a heterocycle containing from one to three heteroatoms selected from N, O, and S.

In some embodiments, p is 2 and n is 2.

In some embodiments, p is 1 and n is 1.

In some embodiments, n is 3.

In some embodiments, L is a bond or $NR_2$ and $R_2$ is H or $CH_3$.

In another aspect, compounds of Formula IIIa are described:

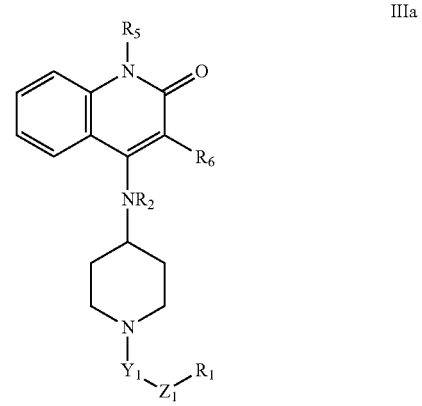

IIIa and pharmaceutically acceptable salts, hydrates, solvates, prodrugs, and tautomers thereof;

wherein $Y_1$ is a bond, —C(O)—, —$CH_2$—, or O;

$Z_1$ is a bond, —C(O)—, —C(O)N($R_3$)(R4), —N($R_3$)(R4), —$SO_2$—, SO, or —$SO_2N(R_3)$(R4);

$R_1$ is selected from the group consisting of a straight chain or branched $C_1$-$C_6$ alkyl, a straight chain or branched $C_2$-$C_6$ alkene;

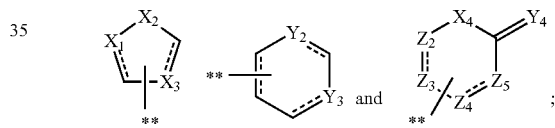

wherein each ------ represents a single or double bond;

each of $X_1$ and $X_3$ is independently CH, O, S, or $NR_2$, provided that when $X_1$ or $X_3$ are attached to a single bond, then each of $X_1$ and $X_3$ is independently $CH_2$, O, S, or $NR_2$;

$X_2$ is $CH_2$, O, S, or $NR_2$, $X_4$ is $NR_2$, $CH_2$, or O;

each of $Y_2$ and $Y_3$ is CH or N; provided that when $Y_2$ or $Y_3$ are attached to a single bond, then each of $Y_2$ and $Y_3$ is independently $CH_2$, or $NR_2$;

$Y_4$ is O or S;

each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently $CH_2$, or $NR_2$; and $R_1$ is optionally substituted;

$R_2$ and $R_5$ are each independently H, —C1-C6 alkyl, —C2-C6 alkene, —(C0-C3 alkyl)-(C3-C6 cycloalkyl), —C(O)C1-C6alkyl, —C(O)NH(C1-C6alkyl), or benzyl; and wherein $R_2$ and $R_5$ are each independently optionally substituted;

$R_3$ and $R_4$ are each independently null, H, —$C_1$-$C_6$ alkyl, —($C_1$-$C_6$alkyl)aryl, aryl, —$C_3$-$C_6$(cycloalkyl); or $R_3$ and $R_4$, when taken together with the nitrogen to which they are attached, can form a heterocycle containing from one to three heteroatoms selected from N, O, and S, and wherein $R_3$ and $R_4$ are optionally substituted; and $R_6$ is an electron withdrawing group.

In some embodiments, R1 is

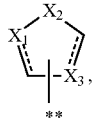

$X_1$ and $X_3$ are each CH; and
each ------ represents a double bond.

In some embodiments, $R_1$ is

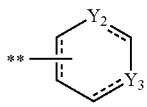

and $Y_3$ is CH and
each ------ represents a double bond.

In some embodiments, $R_6$ is selected from the group consisting of —CN, —NO$_2$, —CO$_2$H, C(O)—Rx, —CO2Rx, and —CO$_2$NRxRy, wherein Rx and Ry are each independently —C$_1$-C$_6$ alkyl, and wherein Rx and Ry, when taken together with the nitrogen to which they are attached, form a heterocycle containing from one to three heteroatoms selected from N, O, and S. In a particular embodiment, $R_6$ is —CN.

In some embodiments, $R_2$ is -cyclopropylmethyl, benzyl, or —CH$_2$CH$_2$OH;

In some embodiments, $R_2$ is H, or CH$_3$.

In another aspect, compounds of Formula IIIb are described:

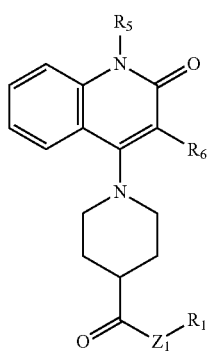

IIIb and pharmaceutically acceptable salts, hydrates, solvates, prodrugs, and tautomers thereof;
wherein $Z_1$ is a bond, CO, CH$_2$, S, O, —N(R3)(R4), —SO2-, or —SO$_2$N(R$_3$)(R4);

$R_1$ selected from the group consisting of null, a straight chain or branched C1-C6 alkyl, a straight chain or branched C2-C6 alkene;

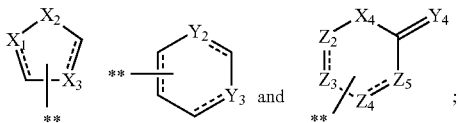

wherein
each ------ represents a single or double bond;
each of $X_1$ and $X_3$ is independently CH, O, S, or NR$_2$, provided that when $X_1$ or $X_3$ are attached to a single bond, then each of $X_1$ and $X_3$ is independently CH$_2$, O, S, or NR$_2$;
$X_2$ is CH$_2$, O, S, or NR$_2$,
$X_4$ is NR$_2$, CH$_2$, or O;
each of $Y_2$ and $Y_3$ is CH or N; provided that when $Y_2$ or $Y_3$ are attached to a single bond, then each of $Y_2$ and $Y_3$ is independently CH$_2$, or NR$_2$;
$Y_4$ is O or S;
each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently CH$_2$, or NR$_2$; and $R_1$ is optionally substituted;

$R_2$ and $R_5$ are each independently H, —C1-C6 alkyl, —C2-C6 alkene, —(C0-C3 alkyl)-(C3-C6 cycloalkyl), —C(O)C1-C6alkyl, —C(O)NH(C1-C6alkyl), or benzyl; and wherein $R_2$ and $R_5$ are each independently optionally substituted;

$R_3$ and $R_4$ are each independently null, H, —C$_1$-C$_6$ alkyl, —(C$_1$-C$_6$alkyl)aryl, aryl, —C$_3$-C$_6$(cycloalkyl); or $R_3$ and $R_4$, when taken together with the nitrogen to which they are attached, can form a heterocycle containing from one to three heteroatoms selected from N, O, and S, and wherein $R_3$ and $R_4$ are optionally substituted; and $R_6$ is an electron withdrawing group.

In some embodiments, R1 is

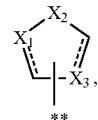

$X_1$ and $X_3$ are each CH; and
each ------ represents a double bond.

In some embodiments, $R_1$ is

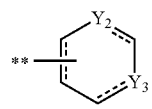

and $Y_3$ is CH and
each ------ represents a double bond.

In some embodiments, $R_6$ is selected from the group consisting of —CN, —NO$_2$, —CO$_2$H, C(O)—Rx, —CO2Rx, and —CO$_2$NRxRy, wherein Rx and Ry are each independently —C$_1$-C$_6$ alkyl, and wherein Rx and Ry, when taken together with the nitrogen to which they are attached, form a heterocycle containing from one to three heteroatoms selected from N, O, and S.

In some embodiments, $Z_1$ is NR$_3$R$_4$, $R_3$ is H and $R_4$ is null.
In some embodiments, $R_6$ is CN.

In another aspect, compounds of Formula IIIc are described:

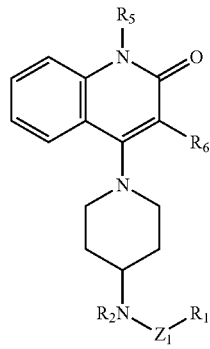

IIIc and pharmaceutically acceptable salts, hydrates, solvates, prodrugs, and tautomers thereof;

wherein $Z_1$ is a bond, S, O, $CH_2$, —C(O)—, —C(O)N($R_3$)(R4), —N(R3)(R4), —SO2—, or —$SO_2$N($R_3$)(R4);

$R_1$ selected from the group consisting of null, a straight chain or branched C1-C6 alkyl, a straight chain or branched C2-C6 alkene;

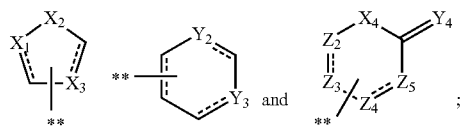

wherein each ------ represents a single or double bond;

each of $X_1$ and $X_3$ is independently CH, O, S, or $NR_2$, provided that when $X_1$ or $X_3$ are attached to a single bond, then each of $X_1$ and $X_3$ is independently $CH_2$, O, S, or $NR_2$;

$X_2$ is $CH_2$, O, S, or $NR_2$;

$X_4$ is $NR_2$, $CH_2$, or O;

each of $Y_2$ and $Y_3$ is CH or N; provided that when $Y_2$ or $Y_3$ are attached to a single bond, then each of $Y_2$ and $Y_3$ is independently $CH_2$, or $NR_2$;

$Y_4$ is O or S;

each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently $CH_2$, or $NR_2$; and $R_1$ is optionally substituted;

$R_2$ and $R_5$ are each independently H, —C1-C6 alkyl, —C2-C6 alkene, —(C0-C3 alkyl)-(C3-C6 cycloalkyl), —C(O)C1-C6alkyl, —C(O)NH(C1-C6alkyl), or benzyl; and wherein $R_2$ and $R_5$ are each independently optionally substituted;

$R_3$ and $R_4$ are each independently null, H, —$C_1$-$C_6$ alkyl, —($C_1$-$C_6$alkyl)aryl, aryl, —$C_3$-$C_6$(cycloalkyl); or $R_3$ and $R_4$, when taken together with the nitrogen to which they are attached, can form a heterocycle containing from one to three heteroatoms selected from N, O, and S, and wherein $R_3$ and $R_4$ are optionally substituted; and $R_6$ is an electron withdrawing group.

In some embodiments, R1 is

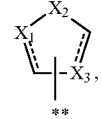

$X_1$ and $X_3$ are each CH; and
each ------ represents a double bond.
In some embodiments, $R_1$ is

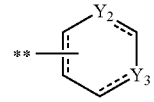

and $Y_3$ is CH and
each ------ represents a double bond.

In some embodiments, $R_6$ is selected from the group consisting of —CN, —$NO_2$, —$CO_2$H, C(O)—Rx, —CO2Rx, and —$CO_2$NRxRy, wherein Rx and Ry are each independently —$C_1$-$C_6$ alkyl, and wherein Rx and Ry, when taken together with the nitrogen to which they are attached, form a heterocycle containing from one to three heteroatoms selected from N, O, and S.

In some embodiments, $R_6$ is CN.

In another aspect, compounds of Formula IIId are described:

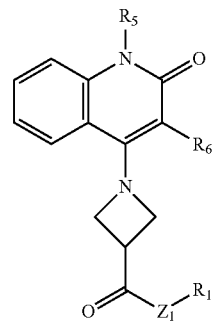

IIId and pharmaceutically acceptable salts, hydrates, solvates, prodrugs, and tautomers thereof;
wherein $Z_1$ is a bond, S, O, or —N($R_3$)($R_4$);

$R_1$ is selected from the group consisting of a straight chain or branched C1-C6 alkyl, a straight chain or branched C2-C6 alkene;

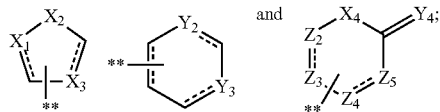

wherein each ------ represents a single or double bond;

each of $X_1$ and $X_3$ is independently CH, O, S, or $NR_2$, provided that when $X_1$ or $X_3$ are attached to a single bond, then each of $X_1$ and $X_3$ is independently $CH_2$, O, S, or $NR_2$;

$X_2$ is $CH_2$, O, S, or $NR_2$;

$X_4$ is $NR_2$, $CH_2$, or O;

each of $Y_2$ and $Y_3$ is CH or N; provided that when $Y_2$ or $Y_3$ are attached to a single bond, then each of $Y_2$ and $Y_3$ is independently $CH_2$, or $NR_2$;

$Y_4$ is O or S;

each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently $CH_2$, or $NR_2$; and $R_1$ is optionally substituted;

$R_2$ and $R_5$ are each independently H, —C1-C6 alkyl, —C2-C6 alkene, —(C0-C3 alkyl)-(C3-C6 cycloalkyl), —C(O)C1-C6alkyl, —C(O)NH(C1-C6alkyl), or benzyl; and wherein $R_2$ and $R_5$ are each independently optionally substituted; and $R_3$ and $R_4$ are each independently null, H, —$C_1$-$C_6$ alkyl, —($C_1$-$C_6$alkyl)aryl, aryl, —$C_3$-$C_6$(cycloalkyl); or $R_3$ and $R_4$, when taken together with the nitrogen to which they are attached, can form a heterocycle containing from one to three heteroatoms selected from N, O, and S, and wherein $R_3$ and $R_4$ are optionally substituted; and $R_6$ is an electron withdrawing group.

In some embodiments, R1 is

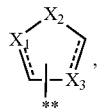

$X_1$ and $X_3$ are each CH; and each ------ represents a double bond.

In some embodiments, $R_1$ is

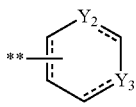

and $Y_3$ is CH and each ------ represents a double bond.

In some embodiments, $R_6$ is selected from the group consisting of —CN, —$NO_2$, —$CO_2H$, C(O)—Rx, —CO2Rx, and —$CO_2$NRxRy, wherein Rx and Ry are each independently —$C_1$-$C_6$ alkyl, and wherein Rx and Ry, when taken together with the nitrogen to which they are attached, form a heterocycle containing from one to three heteroatoms selected from N, O, and S.

In some embodiments, $R_6$ is CN.

In another aspect, compounds of Formula IIIe are described:

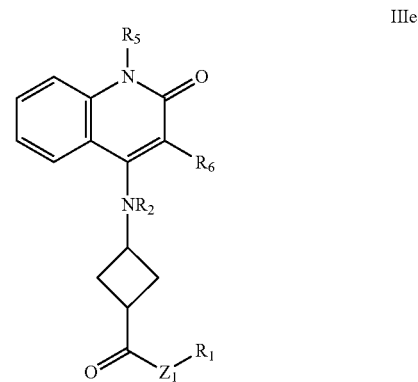

IIIe and pharmaceutically acceptable salts, hydrates, solvates, prodrugs, and tautomers thereof;

wherein $Z_1$ is a bond, O, or —N(R3)(R4);

$R_1$ is selected from the group consisting of a straight chain or branched C1-C6 alkyl, a straight chain or branched C2-C6 alkene;

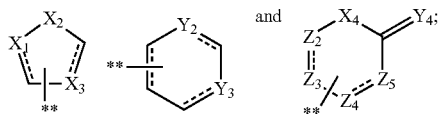

wherein each ------ represents a single or double bond;

each of $X_1$ and $X_3$ is independently CH, O, S, or $NR_2$, provided that when $X_1$ or $X_3$ are attached to a single bond, then each of $X_1$ and $X_3$ is independently $CH_2$, O, S, or $NR_2$;

$X_2$ is $CH_2$, O, S, or $NR_2$;

$X_4$ is $NR_2$, $CH_2$, or O;

each of $Y_2$ and $Y_3$ is CH or N; provided that when $Y_2$ or $Y_3$ are attached to a single bond, then each of $Y_2$ and $Y_3$ is independently $CH_2$, or $NR_2$;

$Y_4$ is O or S;

each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently $CH_2$, or $NR_2$; and $R_1$ is optionally substituted;

$R_2$ and $R_5$ are each independently H, —C1-C6 alkyl, —C2-C6 alkene, —(C0-C3 alkyl)-(C3-C6 cycloalkyl), —C(O)C1-C6alkyl, —C(O)NH(C1-C6alkyl), or benzyl; and wherein $R_2$ and $R_5$ are each independently optionally substituted;

$R_3$ and $R_4$ are each independently null, H, —$C_1$-$C_6$ alkyl, —($C_1$-$C_6$alkyl)aryl, aryl, —$C_3$-$C_6$(cycloalkyl); or $R_3$ and $R_4$, when taken together with the nitrogen to which they are attached, can form a heterocycle containing from one to three heteroatoms selected from N, O, and S, and wherein $R_3$ and $R_4$ are optionally substituted; and $R_6$ is an electron withdrawing group.

In some embodiments, R1 is

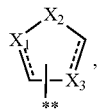

$X_1$ and $X_3$ are each CH; and each ------ represents a double bond.

In some embodiments, $R_1$ is

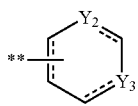

and $Y_3$ is CH and each ------ represents a double bond.

In another aspect, compounds of Formula IIIf are described:

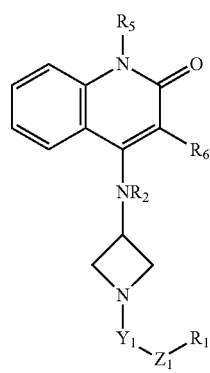

and pharmaceutically acceptable salts, hydrates, solvates, prodrugs, and tautomers thereof;
wherein
$Y_1$ is a bond, —C(O)—, —CH$_2$—, or O;
$Z_1$ is a bond, —C(O)—, —C(O)N(R$_3$)(R4), —N(R$_3$)(R4), —SO$_2$—, or —SO$_2$N(R$_3$)(R4);
$R_1$ selected from the group consisting of a straight chain or branched $C_1$-$C_6$ alkyl, a straight chain or branched C2-C6 alkene;

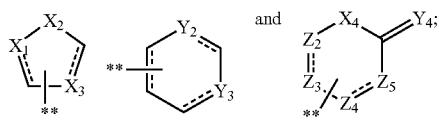

wherein
each ------ represents a single or double bond;
each of $X_1$ and $X_3$ is independently CH, O, S, or NR$_2$, provided that when $X_1$ or $X_3$ are attached to a single bond, then each of $X_1$ and $X_3$ is independently CH$_2$, O, S, or NR$_2$;

$X_2$ is CH$_2$, O, S, or NR$_2$;
$X_4$ is NR$_2$, CH$_2$, or O;
each of $Y_2$ and $Y_3$ is CH or N; provided that when $Y_2$ or $Y_3$ are attached to a single bond, then each of $Y_2$ and $Y_3$ is independently CH$_2$, or NR$_2$,
$Y_4$ is O or S;
each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently CH$_2$, or NR$_2$, and $R_1$ is optionally substituted;

$R_2$ and $R_5$ are each independently H, —C1-C6 alkyl, —C2-C6 alkene, —(C0-C3 alkyl)-(C3-C6 cycloalkyl), —C(O)C1-C6alkyl, —C(O)NH(C1-C6alkyl), or benzyl; and wherein $R_2$ and $R_5$ are each independently optionally substituted;

$R_3$ and $R_4$ are each independently null, H, —C$_1$-C$_6$ alkyl, —(C$_1$-C$_6$alkyl)aryl, aryl, —C$_3$-C$_6$(cycloalkyl); or $R_3$ and $R_4$, when taken together with the nitrogen to which they are attached, can form a heterocycle containing from one to three heteroatoms selected from N, O, and S, and wherein $R_3$ and $R_4$ are optionally substituted; and $R_6$ is an electron withdrawing group.

In some embodiments, R1 is

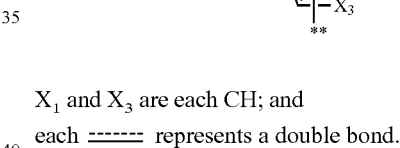

$X_1$ and $X_3$ are each CH; and each ------ represents a double bond.

In some embodiments, $R_1$ is

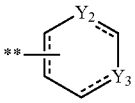

and $Y_3$ is CH and each ------ represents a double bond.

In some embodiments, $R_6$ is selected from the group consisting of —CN, —NO$_2$, —CO$_2$H, C(O)—Rx, —CO2Rx, and —CO$_2$NRxRy, wherein Rx and Ry are each independently —C$_1$-C$_6$ alkyl, and wherein Rx and Ry, when taken together with the nitrogen to which they are attached, form a heterocycle containing from one to three heteroatoms selected from N, O, and S. In a particular embodiment, $R_6$ is —CN.

In some embodiments, $R_2$ is -cyclopropylmethyl, benzyl, or —CH$_2$CH$_2$OH;

In some embodiments, $R_2$ is H, or CH3.

In another aspect, compounds of Formula IIIg are described:

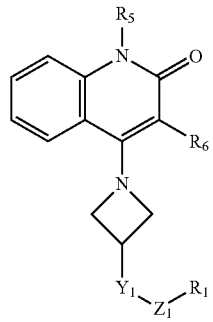

IIIg and pharmaceutically acceptable salts, hydrates, solvates, prodrugs, and tautomers thereof;
wherein $Y_1$ is a bond, —C(O)—, —CH$_2$—, —NR$_2$—, or O;

$Z_1$ is a bond, O, —C(O)—, —C(O)N(R$_3$)(R4), —N(R$_3$)(R4), —SO$_2$—, or —SO$_2$N(R$_3$)(R4);

R$_1$ selected from the group consisting of a straight chain or branched C1-C6 alkyl, a straight chain or branched C2-C6 alkene;

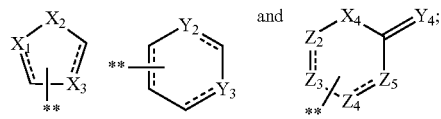

wherein each ------ represents a single or double bond;

each of $X_1$ and $X_3$ is independently CH, O, S, or NR$_2$, provided that when $X_1$ or $X_3$ are attached to a single bond, then each of $X_1$ and $X_3$ is independently CH$_2$, O, S, or NR$_2$;

$X_2$ is CH$_2$, O, S, or NR$_2$;

$X_4$ is NR$_2$, CH$_2$, or O;

each of $Y_2$ and $Y_3$ is CH or N; provided that when $Y_2$ or $Y_3$ are attached to a single bond, then each of $Y_2$ and $Y_3$ is independently CH$_2$, or NR$_2$, $Y_4$ is O or S;

each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently CH$_2$, or NR$_2$; and R$_1$ is optionally substituted;

R$_2$ and R$_5$ are each independently H, —C1-C6 alkyl, —C2-C6 alkene, —(C0-C3 alkyl)-(C3-C6 cycloalkyl), —C(O)C1-C6alkyl, —C(O)NH(C1-C6alkyl), or benzyl; and wherein R$_2$ and R$_5$ are each independently optionally substituted;

R$_3$ and R$_4$ are each independently null, H, —C$_1$-C$_6$ alkyl, —(C$_1$-C$_6$alkyl)aryl, aryl, —C$_3$-C$_6$(cycloalkyl); or R$_3$ and R$_4$, when taken together with the nitrogen to which they are attached, can form a heterocycle containing from one to three heteroatoms selected from N, O, and S, and wherein R$_3$ and R$_4$ are optionally substituted; and R$_6$ is an electron withdrawing group.

In some embodiments, R1 is

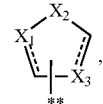

$X_1$ and $X_3$ are each CH; and
each ------ represents a double bond.

In some embodiments, R$_1$ is

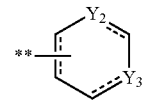

and $Y_3$ is CH and
each ------ represents a double bond.

In some embodiments, R$_2$ is -cyclopropylmethyl, benzyl, or —CH$_2$CH$_2$OH;

In some embodiments, R$_2$ is H, or CH3.

In some embodiments, R$_6$ is selected from the group consisting of —CN, —NO$_2$, —CO$_2$H, C(O)—Rx, —CO$_2$Rx, and —CO$_2$NRxRy, wherein Rx and Ry are each independently —C$_1$-C$_6$ alkyl, and wherein Rx and Ry, when taken together with the nitrogen to which they are attached, form a heterocycle containing from one to three heteroatoms selected from N, O, and S.

In some embodiments, R$_6$ is CN.

In another aspect, pharmaceutical formulations are described comprising at least one MIF inhibitor and a pharmaceutically acceptable carrier.

In another aspect, methods of treating a disease associated with high MIF expression is provided, which comprises administering to a subject in need thereof, a therapeutically-effective amount of a MIF inhibitor. In some embodiments, the disease associated with high MIF expression is selected from Cardiovascular and Cerebrovascular diseases, including but not limited to Atherosclerosis, restenosis of an atherosclerotic coronary artery, Acute coronary syndrome, myocardial infarction, cardiac-allograft vasculopathy, Stroke; Autoimmune Diseases and Inflammatory Disorders, including but not limited to Asthma, chronic obstructive pulmonary disease, Rheumatoid arthritis, Juvenile rheumatoid arthritis, neuropathic pain, Fibromyalgia, Psoriasis, Psoriatic arthritis, colitis, Crohn's disease, ulcerative colitis, Multiple sclerosis, Alzheimer's disease, autoimmune uveitis, Castleman's disease, Ankylosing spondylitis, Pemphigus, Myasthenia gravis, Guillain-Barre syndrome, hepatitis, otitis, experimental allergic neuritis, Autoimmune glomerulonephritis, organ transplant rejection, Sepsis, Shock, spondylitis, systemic lupus erythematosus, lupus nephritis, Diabetes mellitus type 1, Diabetes mellitus type 2, sclerosis, vasculitis, sarcoidosis, pulmonary inflammation, Acute respiratory distress syndrome, wet and dry age-related macular degeneration; Fibrotic diseases; Metabolic disorders, including but not limited to Obesity, steroid-resistance, glucose intolerance, metabolic syndrome; and Neoplasia, including but not limited to angiogenesis, multiple myeloma, leukemia, lymphoma, Hodgkin's disease, cancer of the bone, mouth/pharynx, oesophagus, larynx, stomach, intestine, colon, rectum, lung, liver, pancreas, nerve, brain, head and neck, throat, ovary, uterus, prostate, testis, bladder, kidney, breast non-small cell lung carcinoma, melanoma, skin cancer, teratoma, rhabdomyosarcoma, glioma, metastatic bone disease, and other forms of metastasis.

Also described are methods of inhibiting MIF binding to CD74, CXCR2, CXCR4, and/or other receptors in a subject which comprises administering to a subject in need thereof, a pharmaceutically effective amount of a MIF inhibitor. In some embodiments, the method of inhibiting MIF binding to CD74 includes preventing the interaction between MIF with CD74 alone or MIF with CD74 complexed with CD44, CXCR2, CXCR4 and/or other receptors as receptor signaling heterocomplexes.

Also described are methods of inhibiting MIF-induced activation and signal transduction through CD74, CD44, CXCR2, CXCR4 and/or other receptors in a subject which comprises administering to a subject in need thereof a pharmaceutically effective amount of a MIF inhibitor.

Also described are methods of inhibiting the ability of MIF to form a homomultimer or trimer in a subject which comprises administering to a subject in need thereof a pharmaceutically effective amount of a MIF inhibitor.

Also described are methods of inhibiting MIF tautomerase catalytic activity in a subject which compromises administering to a subject in need thereof a pharmaceutically effective amount of a MIF inhibitor.

Also described are methods of inhibiting MIF biological function in a subject which comprises administering to a subject in need thereof a pharmaceutically effective amount of a MIF inhibitor.

Also described are methods of inhibiting MIF expression, production, and/or secretion in a subject which comprises administering to a subject in need thereof a pharmaceutically effective amount of a MIF inhibitor.

Also described are methods of inhibiting MIF-induced local or systemic inflammatory cell recruitment, infiltration, proliferation or activation; parenchymal cell damage or cellular transformation; or a combination thereof in a subject which comprises administering to a subject in need thereof a pharmaceutically effective amount of a MIF inhibitor.

Also described are methods of inhibiting MIF binding to extracellular and/or intracellular CD74, CXCR2, CXCR4 and/or other targets which comprises contacting a cell with an effective amount of a MIF inhibitor.

Also described are methods of inhibiting MIF binding to soluble receptor forms of CD74, CXCR2, CXCR4 and/or other targets with an effective amount of a MIF inhibitor.

Also described are methods of inhibiting the ability of MIF to form a homomultimer or trimer in the peripheral systemic space, parenchymal space, tissue and/or cell which comprises distributing to or contacting targets in the peripheral systemic space, a parenchymal space, tissue and/or cell with a pharmaceutically effective amount of a MIF inhibitor.

Also described are methods of inhibiting MIF biological function in the peripheral systemic space, parenchymal space, tissue and/or cell which comprises distributing to or contacting targets in the peripheral systemic space, a parenchymal space, tissue and/or cell with a pharmaceutically effective amount of a MIF inhibitor.

Also described are methods of inhibiting MIF expression, production, and/or secretion in a cell which comprises contacting a cell with a pharmaceutically effective amount of a MIF inhibitor.

Also described are methods of inhibiting MIF-induced local and/or systemic inflammatory cell recruitment, infiltration, proliferation or activation; parenchymal cell damage or cellular transformation; or a combination thereof which comprises contacting a cell with an effective amount of a MIF inhibitor.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

DETAILED DESCRIPTION OF THE INVENTION

Based on these emerging data, an in silico screening campaign strategy of known fragment inhibitors coupled with structure-based drug design was conducted to identify lead scaffolds that would inhibit both MIF allosteric and catalytic binding sites and interfere with MIF residues important for receptor binding. Dual pocket binding inhibition is hypothesized to exhibit better potency, efficacy and safety for a competitive inhibitor that differentiates it from single-pocket binding of earlier MIF inhibitors. Multiple interaction points within the two pockets of MIF at the catalytic and allosteric binding sites are expected to enhance potency over single pocket early MIF inhibitors that may translate to more potent inhibition of MIF biological function, production, secretion and its receptor binding. The more complex binding conformation should therefore enhance selectivity resulting in a superior safety profile (lower probability of off-target toxicity) and a wider therapeutic index. Critical MIF residues reportedly important for MIF receptor binding are specifically targeted to inhibit MIF binding with CD74, CXCR2 and/or CXCR4 and downstream signaling events which should translate into improved efficacy and anti-inflammatory effects. Interaction with the newly described surface allosteric pocket in addition to the catalytic domain may more effectively disrupt MIF/receptor binding through physical perturbations and conformational disruption. Fragment-based screening coupled with structure-based drug design using scaffold replacement enabled us to develop in silico new chemical entities incorporating fragment inhibitors that directly bind and inhibit important MIF pharmacophore target sites in single new chemical entities. Novel critical pharmacophoric elements of MIF required for high-affinity binding have only recently been mapped out, thus, not targeted by earlier MIF antagonists.

Definitions

The following definitions are used in connection with the MIF inhibitors:

The term "MIF inhibitor" includes any and all possible isomers, stereoisomers, enantiomers, diastereomers, tautomers, pharmaceutically acceptable salts, hydrates, solvates, and prodrugs of the MIF inhibitors described herein.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted.

"$C_1$-$C_3$ alkyl" refers to a straight or branched chain saturated hydrocarbon containing 1-3 carbon atoms. Examples of a $C_1$-$C_3$ alkyl group include, but are not limited to, methyl, ethyl, propyl and isopropyl.

"$C_1$-$C_4$ alkyl" refers to a straight or branched chain saturated hydrocarbon containing 1-4 carbon atoms. Examples of a $C_1$-$C_4$ alkyl group include, but are not limited to, methyl, ethyl, propyl, butyl, isopropyl, isobutyl, sec-butyl and tert-butyl.

"$C_1$-$C_5$ alkyl" refers to a straight or branched chain saturated hydrocarbon containing 1-5 carbon atoms. Examples of a $C_1$-$C_5$ alkyl group include, but are not limited to, methyl, ethyl, propyl, butyl, pentyl, isopropyl, isobutyl, sec-butyl and tert-butyl, isopentyl and neopentyl.

"$C_1$-$C_6$ alkyl" refers to a straight or branched chain saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, and neopentyl.

The terms "monocyclic or bicyclic aryl," or an "monocyclic or bicyclic heteroaryl" as used herein include but are not limited to, indolyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, dihydropurinonyl, pyrrolopyrimidinyl, purinyl, pyrazolopyridinyl, pyrazolopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, quinolonyl, isoquinolonyl, phthalazinyl, benzodioxyl, indolinyl, benzisobiazoline-1,1, 3-trionyl, dihydroquinolinyl, tetrahydroquinolinyl, dihydroisoquinolyl, tetrahydroisoquinolinyl, benzoazepinyl, benzodiazepinyl, benzoxapinyl, benzoxazepinyl, phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyridinyl, pyrimidinyl, pyrazinyl, pyridazinyl, and triazinyl.

The term "cycloalkyl" refers to a cyclic hydrocarbon containing 3-6 carbon atoms. Examples of a cycloalkyl group include, but are not limited to, cyclopropyl, cyclobutyl, cyclopentyl and cyclohexyl. It is understood that any of the substitutable hydrogens on a cycloalkyl can be substituted with halogen, $C_1$-$C_3$ alkyl, hydroxyl, alkoxy and cyano groups.

The term "heterocycle" as used herein refers to a cyclic hydrocarbon containing 3-6 atoms wherein at least one of the atoms is an O, N, or S wherein a monocyclic heterocycle may contain up to two double bonds. Examples of heterocycles include, but are not limited to, aziridine, oxirane, thiirane, azetidine, oxetane, thietane, pyrrolidine, tetrahydrofuran, tetrahydrothiophene, piperidine, tetrahydropyran, thiane, imidazolidine, oxazolidine, thiazolidine, dioxolane, dithiolane, piperazine, oxazine, dithiane, and dioxane.

A "subject" is a mammal, e.g., a human, mouse, rat, guinea pig, dog, cat, horse, cow, pig, or non-human primate, such as a monkey, chimpanzee, baboon or rhesus, and the terms "subject" and "patient" are used interchangeably herein.

The invention also includes pharmaceutical compositions comprising an effective amount of a MIF inhibitor and a pharmaceutically acceptable carrier. The invention includes a MIF inhibitor provided as a pharmaceutically acceptable prodrug, hydrate, salt, such as a pharmaceutically acceptable salt, enantiomers, stereoisomers, or mixtures thereof.

Representative "pharmaceutically acceptable salts" include, e.g., water-soluble and water-insoluble salts, such as the acetate, amsonate (4,4-diaminostilbene-2, 2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, flunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

An "effective amount" when used in connection with a MIF inhibitor is an amount effective for treating or preventing a MIF-associated disease or disorder.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating", with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a MIF inhibitor.

The term "optionally substituted," as used in this disclosure, means a suitable substituent can replace a hydrogen bound to a carbon, nitrogen, or oxygen. When a substituent is oxo (i.e., =O) then 2 hydrogens on the atom are replaced by a single O. Suitable substituents are selected from the following which include, but are not limited to, hydroxyl, halogen, perfluorinated $C_1$-$C_6$ alkyl, amine, —$C_1$-$C_{12}$ alkyl, —$C_2$-$C_{12}$ alkene, —$C_2$-$C_{12}$ alkyne, —($C_1$-$C_3$ alkyl)-(cycloalkyl), aryl, alkyl-aryl, —C(O)H, —C(O)OH, —C(O)alkyl, —C(O)—O-alkyl, —C(O)NH(alkyl), benzyl, —C(O)NH$_2$, —C(O)N(alkyl)$_2$, —NHC(O)H, —NHC(O)alkyl, —SO$_2$(alkyl), —SO$_2$NH$_2$, —SO$_2$NH(alkyl), —SO$_2$N(alkyl)$_2$, S, CN, and SCN. It will be understood by those skilled in the art, with respect to any group containing one or more substituents, that such groups are not intended to introduce any substitution or substitution patterns that are sterically impractical, synthetically non-feasible and/or inherently unstable. Furthermore, combinations of substituents and/or variables within any of the Formulae represented herein are permissible only if such combinations result in stable compounds or useful synthetic intermediates wherein stable implies a reasonable pharmologically relevant half-life at physiological conditions.

The following abbreviations are used herein and have the indicated definitions: Boc and BOC are tert-butoxycarbonyl, $Boc_2O$ is di-tert-butyl dicarbonate, BSA is bovine serum albumin, CDI is 1,1'-carbonyldiimidazole, DCC is N,N'-dicyclohexylcarbodiimide, DIEA is N,N-diisopropylethylamine, DMAP is 4-dimethylaminopyridine, DMEM is Dulbecco's Modified Eagle Medium, DMF is N,N-dimethylformamide, DOSS is sodium dioctyl sulfosuccinate, EDC and EDCI are 1-ethyl-3-(3-dimethylaminopropyl)carbodiimide hydrochloride, ELISA is enzyme-linked immunosorbent assay, EtOAc is ethyl acetate, FBS is fetal bovine serum, h is hour, HATU is 2-(7-aza-1H-benzotriazole-1-yl)-1,1,3,3-tetramethyluronium hexafluorophosphate, HIV is human immunodeficiency virus, HPMC is hydroxypropyl methylcellulose, oxone is potassium peroxymonosulfate, Pd/C is palladium on carbon, TFA is trifluoroacetic acid, TGPS is tocopherol propylene glycol succinate, and THF is tetrahydrofuran.

Compounds

Accordingly in one aspect, compounds are described that comprise two regions, A and B, linked by a chemical tether, with the A region binding to the allosteric surface binding pocket site and the B region binding to the canonical deep pocket catalytic site. The A region interacts with Tyr36, Trp108, Phe 113 and/or other residues of MIF. Thus A is a substituent capable of pi stacking with Tyr36 causing a rotational displacement of this residue which is critical for effective receptor binding. The B region interacts with a combination of Pro1, Tyr95, Ile64 and/or other residues in the MIF catalytic site through hydrophobic interactions and hydrogen bonding. The tether between the A and B regions of the compound must be of appropriate length and flexibility to allow optimal association with the residues mentioned above while at the same time being rigid enough to maintain conformational integrity needed for initial interaction with the two receptor binding sites. Furthermore the tether is able to form a hydrophobic interaction with Asn97 in the catalytic pocket.

In another aspect, the present invention provides MIF inhibitors according to Formula I:

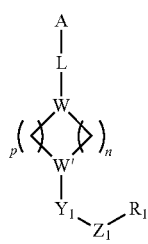

I and pharmaceutically acceptable salts, hydrates, solvates, prodrugs, and tautomers thereof;

wherein A, L, n, p, W, W', $Y_1$, $Z_1$, $R_1$, $R_2$, $R_3$, and $R_4$, are as defined above for Formula I.

In some embodiments, A is an aromatic, bicyclic heterocycle.

In some embodiments, L is a bond.
In some embodiments, L is, —$CH_2$—.
In some embodiments, L is —$NR_2$—.
In some embodiments, L is S.
In some embodiments, L is O.
In some embodiments, each n and p is 1.
In some embodiments, each n and p is 2.
In some embodiments, W is N.
In some embodiments, W is CH.
In some embodiments, W' is N.
In some embodiments, W' is CH.
In some embodiments, $Y_1$ is a bond.
In some embodiments, $Y_1$ is, —C(O)—,
In some embodiments, $Y_1$ is —$CH_2$—.
In some embodiments, $Y_1$ is —$NR_2$—.
In some embodiments, $Y_1$ is O.
In some embodiments, $Z_1$ is a bond.
In some embodiments, $Z_1$ is —C(O)—.
In some embodiments, $Z_1$ is —C(O)N($R_3$)($R_4$).
In some embodiments, $Z_1$ is —N($R_3$)($R_4$).
In some embodiments, $Z_1$ is —$SO_2$—.
In some embodiments, $Z_1$ is —$SO_2$N($R_3$)($R_4$).
In some embodiments, $R_1$ is a straight chain or branched $C_1$-$C_6$ alkyl.
In some embodiments, $R_1$ is a straight chain or branched C2-C6 alkene.
In some embodiments, $R_1$ is aromatic or nonaromatic monocyclic carbocyle.
In some embodiments, $R_1$ is aromatic or nonaromatic monocyclic heterocycle.
In some embodiments, $R_2$ is H.
In some embodiments, $R_2$ is —$C_1$-$C_6$ alkyl.
In some embodiments, $R_2$ is —C2-C6 alkene.
In some embodiments, $R_2$ is —C(O)($C_1$-$C_6$alkyl).
In some embodiments, $R_2$ is —C(O)NH($C_1$-$C_6$alkyl).
In some embodiments, $R_2$ is —($C_0$-$C_3$)—($C_3$-$C_6$)cycloalkyl.
In some embodiments, $R_2$ is or benzyl.
In some embodiments, $R_3$ is a bond.
In some embodiments, $R_3$ is H.
In some embodiments, $R_3$ is —$C_1$-$C_6$ alkyl.
In some embodiments, $R_3$ is —($C_1$-$C_6$alkyl)aryl.
In some embodiments, $R_3$ is aryl.
In some embodiments, $R_3$ is —$C_3$-$C_6$(cycloalkyl).
In some embodiments, $R_3$ and $R_4$, are taken together with the nitrogen to which they are attached and form a heterocycle containing two N.

In some embodiments, A is quinolinyl, isoquinolinyl, phthalazinyl, dihydroquinolinyl, tetrahydroquinolinyl, dihydroisoquinolyl, tetrahydroisoquinolinyl, quinolonyl, isoquinolonyl, or naphthyl, wherein A can be optionally substituted.

In particular embodiments, A is quinolonyl.

In some embodiments, A is pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyridinyl, pyrimidinyl, pyrazinyl, pyridazinyl, or triazinyl, wherein A can be optionally substituted.

In some embodiments, A is selected from the group consisting of

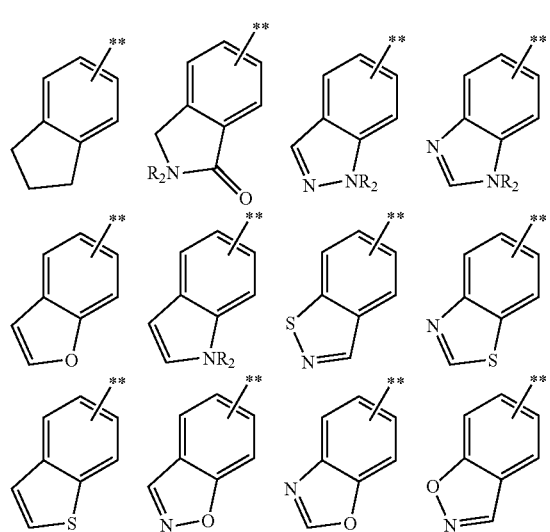

In some embodiments, A is selected from the group consisting of

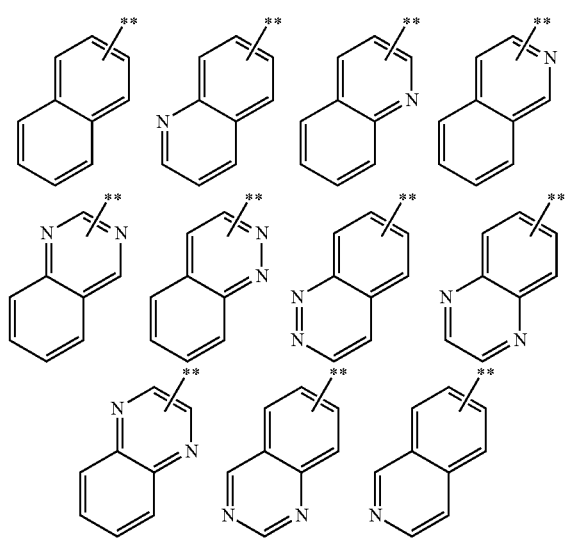

In some embodiments, A is selected from the group consisting of

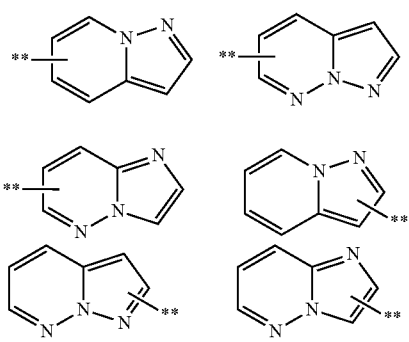

In some embodiments, A is

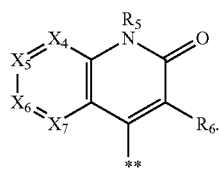

In some embodiments, A is

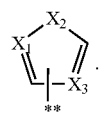

In some embodiments, A is

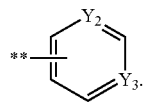

In some embodiments, $X_1$ and $X_3$ are each CH.
In some embodiments, $X_2$ is S.
In some embodiments, $X_2$ is $NR_2$.
In some embodiments, $X_2$ is O.
In some embodiments, $Y_2$ is CH.
In some embodiments, $Y_2$ is N.
In some embodiments, $R_1$ is selected from the group consisting of straight chain or branched C1-C6 alkyl.
In some embodiments, $R_1$ is straight chain or branched C2-C6 alkene.
In some embodiments, $R_1$ is

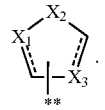

In some embodiments, $R_1$ is

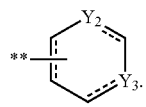

In some embodiments, $R_1$ is

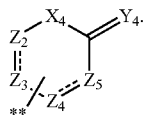

In some embodiments, $X_1$ and $X_3$ are each CH.
In some embodiments, $X_2$ is O.
In some embodiments, $X_2$ is S.
In some embodiments, $X_2$ is $NR_2$.

In some embodiments, $X_4$ is $NR_2$.
In some embodiments, $Y_2$ is CH.
In some embodiments, $Y_2$ is N.
In some embodiments, $Y_4$ is O.
In some embodiments, $Z_2$, $Z_3$, $Z_4$, and $Z_5$ are each CH.
In some embodiments, ------ represents a double bond.
In some embodiments, A is

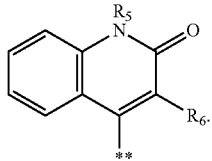

In some embodiments, A is

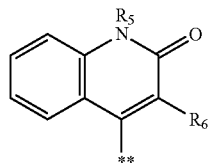

and $R_1$ is

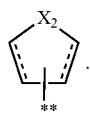

In some embodiments, A is

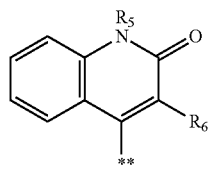

and $R_1$ is

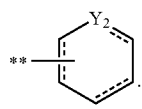

In some embodiments, n is 2 and p is 2.
In some embodiments, W is N and W' is CH.
In some embodiments, n is 1 and p is 1.
In some embodiments, W is CH and W' is N.
In some embodiments, W and W' are each CH.
In some embodiments, $Y_1$ is a bond and Z is —C(O)—.
In some embodiments, L is a bond.
In some embodiments, L is $NR_2$ and $R_2$ is selected from —$C_1$-$C_6$alkyl, benzyl, and —($C_0$-$C_3$)-($C_3$-$C_6$ cycloalkyl), and $R_2$ is optionally substituted.
In some embodiments, $R_2$ is -cyclopropylmethyl, -benzyl or —$CH_2CH_2OH$.
In some embodiments, $R_2$ is selected from H or methyl.

In some embodiments, $R_6$ is —CN.
In some embodiments, $R_5$ is $C_1$-$C_6$ alkyl.
In some embodiments, $R_5$ is $CH_3$.
In some embodiments, $R_5$ is benzyl.

In another aspect, the present invention provides compounds of the Formula II:

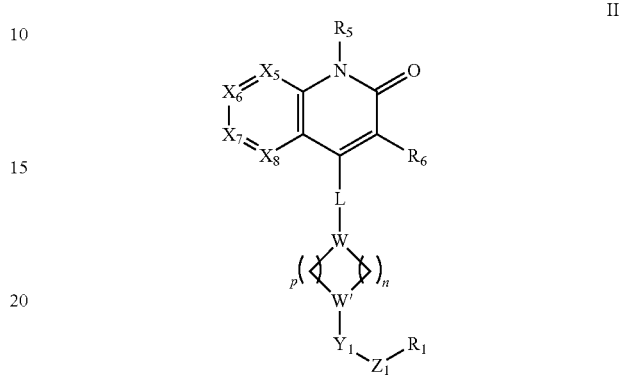

and pharmaceutically acceptable salts, hydrates, solvates, prodrugs, and tautomers thereof;
wherein
$X_5$, $X_6$, $X_7$, and $X_8$ L n and p W and W', $Y_1$, $Z_1$, $R_1$, $R_2$, $R_3$, $R_4$, $R_5$, and $R_6$ are as defined above for Formula II.
In some embodiments, $R_1$ is selected from the group consisting of straight chain or branched C1-C6 alkyl.
In some embodiments, $R_1$ is straight chain or branched C2-C6 alkene.
In some embodiments, $R_1$ is

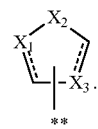

In some embodiments, $R_1$ is

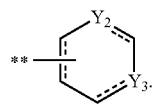

In some embodiments, $R_1$ is

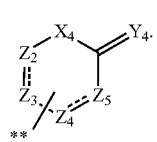

In some embodiments, $X_1$ and $X_3$ are each CH.
In some embodiments, $X_2$ is O.
In some embodiments, $X_2$ is S.
In some embodiments, $X_2$ is $NR_2$.
In some embodiments, $X_4$ is $NR_2$.
In some embodiments, $Y_2$ is CH.
In some embodiments, $Y_2$ is N.

In some embodiments, $Y_4$ is O.
In some embodiments, $Z_2$, $Z_3$, $Z_4$, and $Z_5$ are each CH.
In some embodiments, ------ represents a double bond.
In some embodiments, $R_1$ is

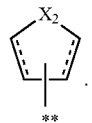

In some embodiments, $R_1$ is

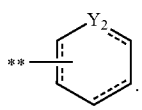

In some embodiments, $R_6$ is —CN.
In some embodiments, p is 2 and n is 2.
In some embodiments, p is 1 and n is 1.
In some embodiments, n is 3.
In some embodiments, L is a bond or $NR_2$ and $R_2$ is H or $CH_3$.

In another aspect, the present invention provides compounds of the Formula IIa:

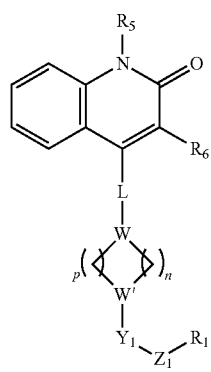

and pharmaceutically acceptable salts, hydrates, solvates, prodrugs, and tautomers thereof;
wherein
L, n, p, W, W', $Y_1$, $Z_1$, $R_1$, $R_2$, $R_3$, $R_4$, $R_5$, and $R_6$ are as defined above for Formula IIa.

In some embodiments, $Y_1$ is a bond.
In some embodiments, $Y_1$ is —$CH_2$—.
In some embodiments, $Y_1$ is —$NR_2$—.
In some embodiments, $Z_1$ is —$N(R_3)(R_4)$.
In some embodiments, $Z_1$ is —$SO_2$—.
In some embodiments, $R_1$ is a straight chain or branched $C_1$-$C_6$ alkyl.

In some embodiments, $R_1$ is straight chain or branched $C_2$-$C_6$ alkene.
In some embodiments, $R_1$ is

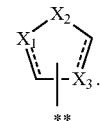

In some embodiments, $R_1$ is

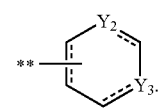

In some embodiments, $R_1$ is

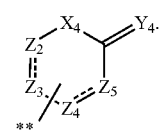

In some embodiments, $X_1$ and $X_3$ are each CH.
In some embodiments, $X_2$ is O.
In some embodiments, $X_2$ is S.
In some embodiments, $X_2$ is $NR_2$.
In some embodiments, $X_4$ is $NR_2$.
In some embodiments, $Y_2$ is CH.
In some embodiments, $Y_2$ is N.
In some embodiments, $Y_4$ is O.
In some embodiments, $Z_2$, $Z_3$, $Z_4$, and $Z_5$ are each CH.
In some embodiments, ------ represents a double bond.
In some embodiments, $R_1$ is

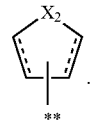

In some embodiments, $R_1$ is

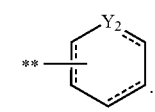

In some embodiments, $R_6$ is —CN.
In some embodiments, p is 2 and n is 2.
In some embodiments, p is 1 and n is 1.
In some embodiments, n is 3.
In some embodiments, L is a bond or $NR_2$ and $R_2$ is H or $CH_3$.

In another aspect, the present invention provides compounds of the Formula III:

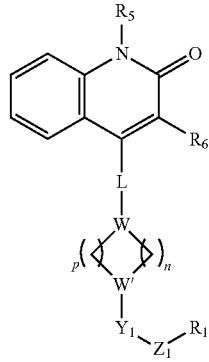

III and pharmaceutically acceptable salts, hydrates, solvates, prodrugs, and tautomers thereof;

wherein L, n, p, W, W', $Y_1$, $Z_1$, $R_1$, $R_2$, $R_5$, and $R_6$ are as defined above for Formula III.

In some embodiments, $Y_1$ is a bond.
In some embodiments, $Y_1$ is —$CH_2$—.
In some embodiments, $Y_1$ is null.
In some embodiments, $Z_1$ is —C(O)—.
In some embodiments, $Z_1$ is —O—.
In some embodiments, $Z_1$ is —N($R_3$)(R4).
In some embodiments, $Z_1$ is a bond.
In some embodiments, $Z_1$ is —S—.
In some embodiments, $Z_1$ is —$CH_2$—.
In some embodiments, $R_1$ is null.
In some embodiments, $R_1$ is a straight chain or branched $C_2$-$C_6$ alkyne.
In some embodiments, $R_1$ is a substituted straight chain or branched $C_2$-$C_6$ alkyne.
In some embodiments, $R_1$ is a CN.
In some embodiments, $R_1$ is a straight chain or branched $C_2$-$C_6$ alkene.
In some embodiments, $R_1$ is a substituted straight chain or branched $C_2$-$C_6$ alkene.
In some embodiments, $R_1$ is a straight chain or branched $C_1$-$C_6$ alkyl.
In some embodiments, $R_1$ is a substituted straight chain or branched $C_1$-$C_6$ alkyl.
In some embodiments, $R_1$ is a nonaromatic monocyclic heterocycle.
In some embodiments, $R_1$ is a substituted nonaromatic monocyclic heterocycle.
In some embodiments, $R_1$ is a aromatic monocyclic heterocycle.
In some embodiments, $R_1$ is a substituted aromatic monocyclic heterocycle.
In some embodiments, $R_1$ is an aromatic or nonaromatic monocyclic carbocycle.
In some embodiments, $R_1$ is a substituted aromatic or nonaromatic monocyclic carbocycle.

In some embodiments, $R_1$ is

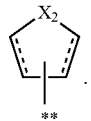

In some embodiments, $R_1$ is

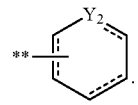

In some embodiments, $R_6$ is —CN.
In some embodiments, p is 2 and n is 2.
In some embodiments, p is 1 and n is 1.
In some embodiments, n is 3.
In some embodiments, L is a bond or $NR_2$ and $R_2$ is H or $CH_3$.

In another aspect, the present invention provides compounds of the Formula IIIa:

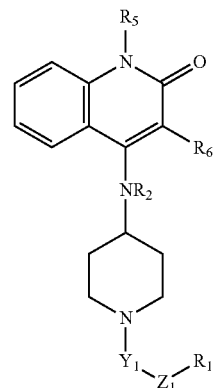

IIIa and pharmaceutically acceptable salts, hydrates, solvates, prodrugs, and tautomers thereof;

wherein $Y_1$, $Z_1$, $R_1$, $R_2$, $R_5$, and $R_6$ are as defined above for Formula IIIa.

In some embodiments, $Y_1$ is a bond.
In some embodiments, $Y_1$ is —$CH_2$—.
In some embodiments, $Z_1$ is a bond.
In some embodiments, $Z_1$ is —C(O)—.
In some embodiments, $Z_1$ is a —S(O)—.
In some embodiments, $Z_1$ is —S($O_2$)—.
In some embodiments, $R_1$ is a substituted straight chain or branched $C_1$-$C_6$ alkyl.
In some embodiments, $R_1$ is a straight chain or branched $C_2$-$C_6$ alkene.
In some embodiments, $R_1$ is a straight chain or branched $C_2$-$C_6$ alkyne.
In some embodiments, $R_1$ is a $C_3$-$C_4$ cyclic alkyl.

In some embodiments, $R_1$ is

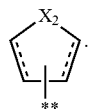

In some embodiments, $R_1$ is

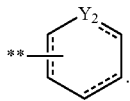

In some embodiments, $R_6$ is —CN.

In other illustrative embodiments, compounds of Formula IIIa are as set forth below:

1-methyl-2-oxo-4-(1-(thiophene-2-carbonyl)piperidin-4-ylamino)-1,2-dihydroquinoline-3-carbonitrile (IIIa-1);

4-(1-benzoylpiperidin-4-ylamino)-1-methyl-2-oxo-1,2-dihydroquinoline-3-carbonitrile (IIIa-2);

4-(3-cyano-1-methyl-2-oxo-1,2-dihydroquinolin-4-ylamino)-N-phenylpiperidine-1-carboxamide (IIIa-3);

4-(1-(2-hydroxyacetyl)piperidin-4-ylamino)-1-methyl-2-oxo-1,2-dihydroquinoline-3-carbonitrile (IIIa-4);

4-(1-benzylpiperidin-4-ylamino)-1-methyl-2-oxo-1,2-dihydroquinoline-3-carbonitrile (IIIa-5);

1-methyl-4-(methyl(1-(thiophene-2-carbonyl)piperidin-4-yl)amino)-2-oxo-1,2-dihydroquinoline-3-carbonitrile (IIIa-6);

1-(4-fluorobenzyl)-2-oxo-4-(1-(thiophene-2-carbonyl)piperidin-4-ylamino)-1,2-dihydroquinoline-3-carbonitrile (IIIa-7);

4-(1-(2-hydroxyethyl)piperidin-4-ylamino)-1-methyl-2-oxo-1,2-dihydroquinoline-3-carbonitrile (IIIa-8);

4-(1-(4-fluorobenzoyl)piperidin-4-ylamino)-1-methyl-2-oxo-1,2-dihydroquinoline-3-carbonitrile (IIIa-9); and 1-benzyl-2-oxo-4-(1-(thiophene-2-carbonyl)piperidin-4-ylamino)-1,2-dihydroquinoline-3-carbonitrile (IIIc-10).

In another aspect, the present invention provides compounds of Formula IIIb:

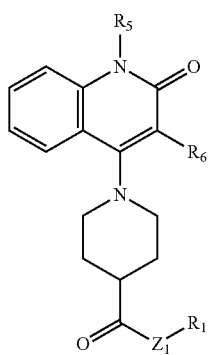

IIIb and pharmaceutically acceptable salts, hydrates, solvates, prodrugs, and tautomers thereof;

wherein $Z_1$, $R_1$, $R_2$, $R_5$, and $R_6$ are as defined above for Formula IIIb.

In some embodiments, $Z_1$ is —N($R_3$)(R4).

In some embodiments, $Z_1$ is —O—.

In some embodiments, $Z_1$ is —S—.

In some embodiments, $R_1$ is CN.

In some embodiments, $R_1$ is a straight chain or branched $C_1$-$C_6$ alkyl.

In some embodiments, $R_1$ is a substituted straight chain or branched $C_1$-$C_6$ alkyl.

In some embodiments, $R_1$ is an aromatic or nonaromatic monocyclic heterocycle.

In some embodiments, $R_1$ is a substituted aromatic or non-aromatic monocyclic heterocycle.

In some embodiments, $R_1$ is

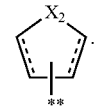

In some embodiments, $R_1$ is

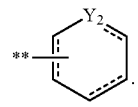

In some embodiments, $R_6$ is —CN.

In some embodiments, $Z_1$ is NH.

In other illustrative embodiments, compounds of Formula IIIb are as set forth below:

1-methyl-2-oxo-4-(4-(thiophene-2-carbonyl)piperidin-1-yl)-1,2-dihydroquinoline-3-carbonitrile (IIIb-1);

1-(3-cyano-1-methyl-2-oxo-1,2-dihydroquinolin-4-yl)-N-(4-fluorophenyl)piperidine-4-carboxamide (IIIb-2);

1-(3-cyano-1-methyl-2-oxo-1,2-dihydroquinolin-4-yl)-N-(2-hydroxyethyl)piperidine-4-carboxamide (IIIb-3);

1-(3-cyano-1-(4-fluorobenzyl)-2-oxo-1,2-dihydroquinolin-4-yl)-N-phenylppiperidine-4-carboxamide (IIIb-4);

1-(3-cyano-1-methyl-2-oxo-1,2-dihydroquinolin-4-yl)-N-(thiophen-2-yl)piperidine-4-carboxamide (IIIb-5);

1-(3-cyano-1-methyl-2-oxo-1,2-dihydroquinolin-4-yl)-N-phenylpiperidine-4-carboxamide (IIIb-6);

1-(3-cyano-1-methyl-2-oxo-1,2-dihydroquinolin-4-yl)-N-(pyridin-4-yl)piperidine-4-carboxamide (IIIb-7);

1-(3-cyano-1-methyl-2-oxo-1,2-dihydroquinolin-4-yl)-N-(tetrahydrofuran-3-yl)piperidine-4-carboxamide (IIIb-8);

1-(3-cyano-1-methyl-2-oxo-1,2-dihydroquinolin-4-yl)-N-(thiophen-3-yl)piperidine-4-carboxamide (IIIb-9); and 1-(1-benzyl-3-cyano-2-oxo-1,2-dihydroquinolin-4-yl)-N-(thiophen-2-yl)piperidine-4-carboxamide (IIIb-10).

In another aspect, the present invention provides compounds of Formula IIIc:

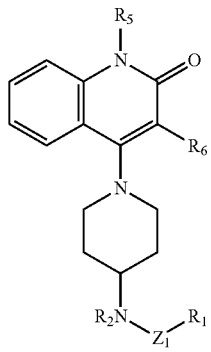

and pharmaceutically acceptable salts, hydrates, solvates, prodrugs, and tautomers thereof;
wherein $Z_1$ $R_1$ $R_2$, $R_5$, $R_6$ are as defined above for Formula IIIc.

In some embodiments, $Z_1$ is —C(O)—.
In some embodiments, $Z_1$ is —SO$_2$.
In some embodiments, $R_1$ is a straight chain or branched $C_1$-$C_6$ alkyl.
In some embodiments, $R_1$ is a substituted straight chain or branched $C_1$-$C_6$ alkyl.
In some embodiments, $R_1$ is a straight chain or branched $C_2$-$C_6$ alkene.
In some embodiments, $R_1$ is a substituted straight chain or branched $C_2$-$C_6$ alkene.
In some embodiments, $R_1$ is a straight chain or branched $C_2$-$C_6$ alkyne.
In some embodiments, $R_1$ is a substituted straight chain or branched $C_2$-$C_6$ alkyne.
In some embodiments, $R_1$ is a substituted nonaromatic monocyclic carbocycle.
In some embodiments, $R_1$ is

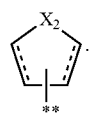

In some embodiments, $R_1$ is

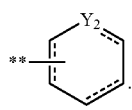

In some embodiments, $R_6$ is —CN.
In other illustrative embodiments, compounds of Formula IIIc are as set forth below:
N-(1-(3-cyano-1-methyl-2-oxo-1,2-dihydroquinolin-4-yl)piperidin-4-yl)thiophene-2-carboxamide (IIIc-1);
N-(1-(3-cyano-1-methyl-2-oxo-1,2-dihydroquinolin-4-yl)piperidin-4-yl)benzamide (IIIc-2);
1-(1-(3-cyano-1-methyl-2-oxo-1,2-dihydroquinolin-4-yl)piperidin-4-yl)-3-(thiophen-2-yl)urea (IIIc-3);
N-(1-(3-cyano-1-methyl-2-oxo-1,2-dihydroquinolin-4-yl)piperidin-4-yl)-N-methylthiophene-2-carboxamide (IIIc-4);
N-(1-(3-cyano-1-methyl-2-oxo-1,2-dihydroquinolin-4-yl)piperidin-4-yl)-2-hydroxyacetamide (IIIc-5);
N-(1-(3-cyano-1-(4-fluorobenzyl)-2-oxo-1,2-dihydroquinolin-4-yl)piperidin-4-yl)thiophene-2-carboxamide (IIIc-6);
N-(1-(1-benzyl-3-cyano-2-oxo-1,2-dihydroquinolin-4-yl)piperidin-4-yl)thiophene-2-carboxamide (IIIc-7);
N-(1-(3-cyano-1-methyl-2-oxo-1,2-dihydroquinolin-4-yl)piperidin-4-yl)-4-(hydroxymethyl)benzamide (IIIc-8);
4-(4-(2-hydroxyethylamino)piperidin-1-yl)-1-methyl-2-oxo-1,2-dihydroquinoline-3-carbonitrile (IIIc-9); and
N-(1-(3-cyano-1-methyl-2-oxo-1,2-dihydroquinolin-4-yl)piperidin-4-yl)tetrahydrofuran-3-carboxamide (IIIc-10).

In another aspect, the present invention provides compounds of the Formula IIId:

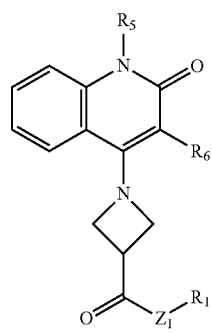

and pharmaceutically acceptable salts, hydrates, solvates, prodrugs, and tautomers thereof;
wherein $R_1$, $R_2$, $R_5$, and $R_6$ are as defined above for Formula IIId.

In some embodiments $Z_1$ is a bond.
In some embodiments $Z_1$ is —S—.
In some embodiments $Z_1$ is —N($R_3$)($R_4$).
In some embodiments, $R_1$ is a straight chain or branched $C_1$-$C_6$ alkyl.
In some embodiments, $R_1$ is a straight chain or branched $C_2$-$C_6$ alkene.
In some embodiments, $R_1$ is a straight chain or branched $C_2$-$C_6$ alkyne.
In some embodiments, $R_1$ is

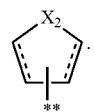

In some embodiments, $R_1$ is

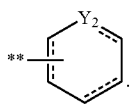

In some embodiments, $R_6$ is —CN.
In other illustrative embodiments, compounds of Formula IIId are as set forth below:
1-(3-cyano-1-methyl-2-oxo-1,2-dihydroquinolin-4-yl)-N-(thiophen-2-yl)azetidine-3-carboxamide (IIId-1);
1-(3-cyano-1-methyl-2-oxo-1,2-dihydroquinolin-4-yl)-N-phenylazetidine-3-carboxamide (IIId-2);

N-benzyl-1-(3-cyano-1-methyl-2-oxo-1,2-dihydroquinolin-4-yl)azetidine-3-carboxamide (IIId-3);
1-(3-cyano-1-methyl-2-oxo-1,2-dihydroquinolin-4-yl)-N-(2-hydroxyethyl)azetidine-3-carboxamide (IIId-4);
N-allyl-1-(3-cyano-1-methyl-2-oxo-1,2-dihydroquinolin-4-yl)azetidine-3-carboxamide (IIId-5);
1-(1-benzyl-3-cyano-2-oxo-1,2-dihydroquinolin-4-yl)-N-(thiophen-2-yl)azetidine-3-carboxamide (IIId-6);
1-(3-cyano-1-(4-fluorobenzyl)-2-oxo-1,2-dihydroquinolin-4-yl)-N-(thiophen-2-yl)azetidine-3-carboxamide (IIId-7);
1-(3-cyano-1-methyl-2-oxo-1,2-dihydroquinolin-4-yl)-N-(4-hydroxyphenyl)azetidine-3-carboxamide (IIId-8);
1-(3-cyano-1-methyl-2-oxo-1,2-dihydroquinolin-4-yl)-N-(4-hydroxybenzyl)azetidine-3-carboxamide (IIId-9); and
1-(3-cyano-1-methyl-2-oxo-1,2-dihydroquinolin-4-yl)-N-(tetrahydrofuran-3-yl)azetidine-3-carboxamide (IIId-10).

In another aspect, the present invention provides compounds of the Formula IIIe:

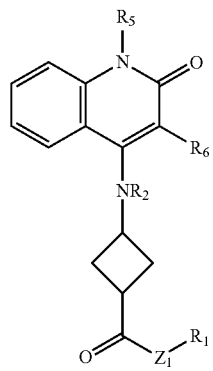

and pharmaceutically acceptable salts, hydrates, solvates, prodrugs, and tautomers thereof;
wherein $Z_1$, $R_1$, $R_2$, $R_5$, and $R_6$ are as defined above for Formula IIIe.

In some embodiments, $Z_1$ is a bond.
In some embodiments, $Z_1$ is —N($R_3$)($R_4$).
In some embodiments, $R_1$ is a straight chain or branched $C_1$-$C_6$ alkyl.
In some embodiments, $R_1$ is a straight chain or branched $C_2$-$C_6$ alkene.
In some embodiments, $R_1$ is, a straight chain or branched $C_2$-$C_6$ alkyne.
In some embodiments, $R_1$ is

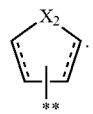

In some embodiments, $R_1$ is

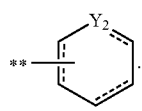

In some embodiments, $R_6$ is —CN.
In other illustrative embodiments, compounds of Formula IIIe are as set forth below:
3-(1-benzyl-3-cyano-2-oxo-1,2-dihydroquinolin-4-ylamino)-N-(thiophen-2-yl)cyclobutanecarboxamide (IIIe-1);
3-(3-cyano-1-methyl-2-oxo-1,2-dihydroquinolin-4-ylamino)-N-(thiophen-2-yl)cyclobutanecarboxamide (IIIe-2);
3-(3-cyano-1-(4-fluorobenzyl)-2-oxo-1,2-dihydroquinolin-4-ylamino)-N-(thiophen-2-yl)cyclobutanecarboxamide (IIIe-3);
3-(3-cyano-1-methyl-2-oxo-1,2-dihydroquinolin-4-ylamino)-N-(tetrahydrofuran-3-yl)cyclobutanecarboxamide (IIIe-4);
N-benzyl-3-(3-cyano-1-methyl-2-oxo-1,2-dihydroquinolin-4-ylamino)cyclobutanecarboxamide (IIIe-5);
3-(3-cyano-1-methyl-2-oxo-1,2-dihydroquinolin-4-ylamino)-N-phenylcyclobutanecarboxamide (IIIe-6);
3-(3-cyano-1-methyl-2-oxo-1,2-dihydroquinolin-4-ylamino)-N-(2-hydroxyethyl)cyclobutanecarboxamide (IIIe-7); and
3-((3-cyano-1-methyl-2-oxo-1,2-dihydroquinolin-4-yl)(methyl)amino)-N-(thiophen-2-yl)cyclobutanecarboxamide (IIIe-8).

In another aspect, compounds of Formula IIIf are described:

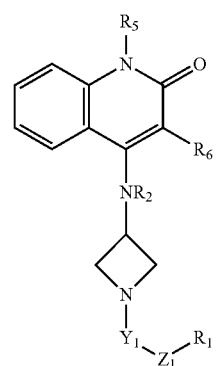

and pharmaceutically acceptable salts, hydrates, solvates, prodrugs, and tautomers thereof;
wherein $X_1$, $X_2$, $X_3$, $Y_1$, $Y_2$, $Y_3$, $Y_4$, $Z_1$, $Z_2$, $Z_3$, $Z_4$, $Z_5$, $R_1$, $R_2$, $R_3$, $R_4$, $R_5$, and $R_6$, are as defined above for Formula IIIf.

In some embodiments, R1 is

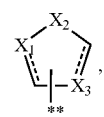

$X_1$ and $X_3$ are each CH; and
each ------ represents a double bond.
In some embodiments, $R_1$ is

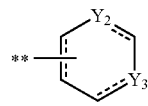

and $Y_3$ is CH and
each ------ represents a double bond.
In some embodiments, $R_6$ is selected from the group consisting of —CN, —NO$_2$, —CO$_2$H, C(O)—Rx, —CO$_2$Rx, and —CO$_2$NRxRy, wherein Rx and Ry are each independently —C$_1$-C$_6$ alkyl, and wherein Rx and Ry, when taken together with the nitrogen to which they are attached, form a heterocycle containing from one to three heteroatoms selected from N, O, and S. In a particular embodiment, $R_6$ is —CN.

In some embodiments, $R_2$ is -cyclopropylmethyl, benzyl, or —$CH_2CH_2OH$;

In some embodiments, $R_2$ is H, or CH3.

In other illustrative embodiments, compounds of Formula IIIf are as set forth below:

1-methyl-2-oxo-4-(1-(thiophene-2-carbonyl)azetidin-3-ylamino)-1,2-dihydroquinoline-3-carbonitrile XXIV, (IIIf-1)

1-methyl-4-(1-(methylsulfonyl)azetidin-3-ylamino)-2-oxo-1,2-dihydroquinoline-3-carbonitrile XXVI, (IIIf-2), and 1-(4-fluorobenzyl)-2-oxo-4-(1-(thiophen-2-ylsulfonyl)azetidin-3-ylamino)-1,2-dihydroquinoline-3-carbonitrile XXXIV, (IIIf-3).

In another aspect, compounds of Formula IIIg are described:

IIIg and pharmaceutically acceptable salts, hydrates, solvates, prodrugs, and tautomers thereof;

wherein $X_1$, $X_2$, $X_3$, $Y_1$, $Y_2$, $Y_3$, $Y_4$, $Z_1$, $Z_2$, $Z_3$, $Z_4$, $Z_5$, $R_1$, $R_2$, $R_3$, $R_4$, $R_5$, and $R_6$, are as defined above for Formula IIIg.

In some embodiments, R1 is $X_1$ and $X_3$ are each CH; and each ------ represents a double bond.

In some embodiments, $R_1$ is and $Y_3$ is CH and each ------ represents a double bond.

In some embodiments, $R_6$ is selected from the group consisting of —CN, —$NO_2$, —$CO_2H$, C(O)—Rx, —CO2Rx, and —$CO_2$NRxRy, wherein Rx and Ry are each independently —$C_1$-$C_6$ alkyl, and wherein Rx and Ry, when taken together with the nitrogen to which they are attached, form a heterocycle containing from one to three heteroatoms selected from N, O, and S. In a particular embodiment, $R_6$ is —N.

In some embodiments, $R_2$ is -cyclopropylmethyl, benzyl, or —$CH_2CH_2OH$;

In some embodiments, $R_2$ is H, or CH3.

In other illustrative embodiments, compounds of Formula IIIg are as set forth below:

N-[1-(3-cyano-1-methyl-2-oxo-1,2-dihydroquinolin-4-yl)azetidin-3-yl]thiophene-2-carboxamide, compound XXI, (IIIg-1), 1-methyl-2-oxo-4-(1-(thiophene-2-carbonyl)azetidin-3-ylamino)-1,2-dihydroquinoline-3-carbonitrile XXVII, (IIIg-2), and 1-methyl-2-oxo-4-[4-(thiophen-2-ylcarbonyl)azetidin-3-yl]-1,2-dihydroquinoline-3-carbonitrile; compound V, (IIIg-3)

Methods for Making the MIF Inhibitors

Examples of synthetic pathways useful for making MIF inhibitors of Formulae I, II, IIa, III, IIIa, IIIb, IIIc, IIId, IIIe, IIIf, and IIIg are set forth in the Examples below and generalized in Scheme 1.

Scheme 1

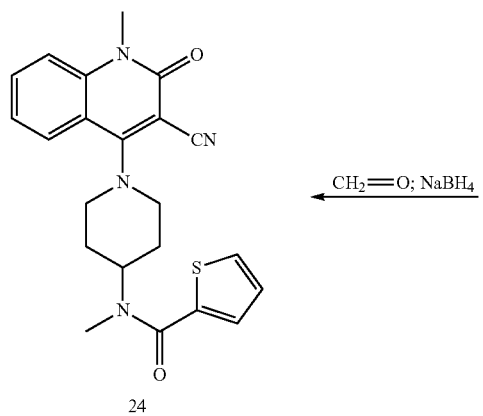 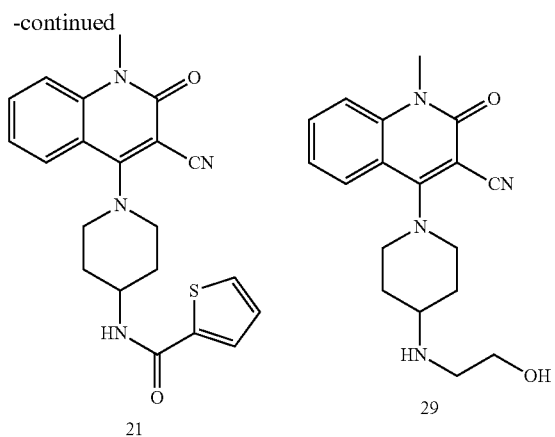

Exposure of Intermediate I, which is prepared according to WO2006199825, to a suitably protected amine in the presence of an amine base such as triethylamine or diisopropylethyl amine in a aprotic solvent followed by removal of the protecting group yields an intermediate of type II. Reaction of II with a carbonyl source such as carbonyl diimidazole followed by addition of an amine such as aminothiazole gives urea 23. Reaction of intermediate II with substituted carboxylic acids, such a 2-thiazolecarboxylic acid, in the presence of an amine base such as triethylamine and typical coupling reagents such as EDC gives rise to amides such as thiazole amide 21. Reaction of amide 21 under Eschweiler Clark conditions gives rise to tertiary amine 24. Reaction of intermediate II with a substituted aldehyde, such as 2-hydroxyacetaldehyde, under reductive amination conditions using sodium borohydride or sodium triacetoxyborohydride gives rise to substituted amines such as hydroxylamine 29.

Methods for Using MIF Inhibitors

In another aspect, methods of treating a disease associated with high MIF expression is provided, which comprises administering to a subject in need thereof, a therapeutically-effective amount of a MIF inhibitor. In some embodiments, the disease associated with high MIF expression is selected from Cardiovascular and Cerebrovascular diseases, including but not limited to Atherosclerosis, restenosis of an atherosclerotic coronary artery, Acute coronary syndrome, myocardial infarction, cardiac-allograft vasculopathy, Stroke; Autoimmune Diseases and Inflammatory Disorders, including but not limited to Asthma, chronic obstructive pulmonary disease, Rheumatoid arthritis, Juvenile rheumatoid arthritis, neuropathic pain, Fibromyalgia, Psoriasis, Psoriatic arthritis, colitis, Crohn's disease, ulcerative colitis, Multiple sclerosis, Alzheimer's disease, autoimmune uveitis, Castleman's disease, Ankylosing spondylitis, Pemphigus, Myasthenia gravis, Guillain-Barre syndrome, hepatitis, otitis, experimental allergic neuritis, Autoimmune glomerulonephritis, organ transplant rejection, Sepsis, Shock, spondylitis, systemic lupus erythematosus, lupus nephritis, Diabetes mellitus type 1, Diabetes mellitus type 2, sclerosis, vasculitis, sarcoidosis, pulmonary inflammation, Acute respiratory distress syndrome, wet and dry age-related macular degeneration; Fibrotic diseases; Metabolic disorders, including but not limited to Obesity, steroid-resistance, glucose intolerance, metabolic syndrome; and Neoplasia, including but not limited to angiogenesis, multiple myeloma, leukemia, lymphoma, Hodgkin's disease, cancer of the bone, mouth/pharynx, oesophagus, larynx, stomach, intestine, colon, rectum, lung, liver, pancreas, nerve, brain, head and neck, throat, ovary, uterus, prostate, testis, bladder, kidney, breast, non-small cell lung carcinoma, melanoma, skin cancer, teratoma, rhabdomyosarcoma, glioma, metastatic bone disease and other forms of metastasis.

Also described are methods of inhibiting MIF binding to CD74 in a subject which comprises administering to a subject in need thereof, a pharmaceutically effective amount of a MIF inhibitor. In some embodiments, the method of inhibiting MIF binding to CD74 includes preventing the interaction between MIF with CD74 alone or MIF with CD74 complexed with CD44, CXCR2, CXCR4 and/or other receptors as receptor signaling heterocomplexes.

Also described are methods of inhibiting MIF-induced activation and signal transduction through CD74, CD44, CXCR2, CXCR4 and/or other receptors in a subject which comprises administering to a subject in need thereof a pharmaceutically effective amount of a MIF inhibitor.

Also described are methods of inhibiting the ability of MIF to form a homomultimer or trimer in a subject which comprises administering to a subject in need thereof a pharmaceutically effective amount of a MIF inhibitor.

Also described are methods of inhibiting MIF tautomerase catalytic activity in a subject which comprises administering to a subject in need thereof a pharmaceutically effective amount of a MIF inhibitor.

Also described are methods of inhibiting MIF biological function in a subject which comprises administering to a subject in need thereof a pharmaceutically effective amount of a MIF inhibitor.

Also described are methods of inhibiting MIF expression, production, and/or secretion in a subject which comprises administering to a subject in need thereof a pharmaceutically effective amount of a MIF inhibitor.

Also described are methods of inhibiting MIF-induced local or systemic inflammatory cell recruitment, infiltration, proliferation or activation; parenchymal cell damage or cellular transformation; or a combination thereof in a subject which comprises administering to a subject in need thereof a pharmaceutically effective amount of a MIF inhibitor.

Also described are methods of inhibiting MIF binding to extracellular and/or intracellular CD74, CXCR2, CXCR4 and/or other targets which comprises contacting a cell with an effective amount of a MIF inhibitor.

Also described are methods of inhibiting MIF binding to soluble receptor forms of CD74, CXCR2, CXCR4 and/or other targets with an effective amount of a MIF inhibitor.

Also described are methods of inhibiting the ability of MIF to form a homomultimer or trimer in the peripheral systemic space, parenchymal space, tissue and/or cell which comprises distributing to or contacting targets in the peripheral systemic space, a parenchymal space, tissue and/or cell with a pharmaceutically effective amount of a MIF inhibitor.

Also described are methods of inhibiting MIF biological function in the peripheral systemic space, parenchymal space, tissue and/or cell which comprises distributing to or contacting targets in the peripheral systemic space, a parenchymal space, tissue and/or cell with a pharmaceutically effective amount of a MIF inhibitor.

Also described are methods of inhibiting MIF expression, production, and/or secretion in a cell which comprises contacting a cell with a pharmaceutically effective amount of a MIF inhibitor.

Also described are methods of inhibiting MIF-induced local and/or systemic inflammatory cell recruitment, infiltration, proliferation or activation; parenchymal cell damage or cellular transformation; or a combination thereof which comprises contacting a cell with an effective amount of a MIF inhibitor.

Also provided in the invention is a method for inhibiting, preventing, or treating a disease, or symptoms of a MIF related disease, in a subject. Examples of such disorders include, but are not limited to Cardiovascular and Cerebrovascular diseases, Autoimmune Diseases and Inflammatory Disorders, Fibrotic diseases, Metabolic disorders, and Oncologic diseases.

In some embodiments, the subject is administered an effective amount of a MIF inhibitor.

The invention also includes pharmaceutical compositions useful for treating or preventing a MIF associated disease, or for inhibiting a MIF associated disease, or more than one of these activities. The compositions can be suitable for internal use and comprise an effective amount of a MIF inhibitor and a pharmaceutically acceptable carrier. The MIF inhibitors are especially useful in that they demonstrate very low systemic toxicity or no systemic toxicity.

The MIF inhibitors can each be administered in amounts that are sufficient to treat or prevent but are not limited to Cardiovascular and Cerebrovascular diseases, Autoimmune Diseases and Inflammatory Disorders, Fibrotic diseases, Metabolic disorders, and Oncologic diseases or prevent the development thereof in subjects.

Administration of the MIF inhibitors can be accomplished via any mode of administration for therapeutic agents. These modes include systemic or local administration such as oral, nasal, parenteral (intravenous), intramuscular, intrathecal, intra-vitreal, transdermal, subcutaneous, vaginal, buccal, rectal, topical administration modes or as a drug-eluting stent.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, intrathecal, intra-vitreal injection, subcutaneous or intramuscular form, all using forms well known to those skilled in the pharmaceutical arts.

Illustrative pharmaceutical compositions are tablets and gelatin capsules comprising a MIF inhibitor and a pharmaceutically acceptable carrier, such as: a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the MIF inhibitor is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the MIF inhibitors.

The MIF inhibitors can be also formulated as a suppository that can be prepared from fatty emulsions or suspensions; using polyalkylene glycols such as propylene glycol, as the carrier.

In further embodiments, the pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, delayed release formulations, extended release formulations, pulsatile release formulations, multiparticulate formulations, and mixed immediate and controlled release formulations The MIF inhibitors can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564, the contents of which are herein incorporated by reference in their entirety.

MIF inhibitors can also be delivered by the use of monoclonal antibodies as individual carriers to which the MIF inhibitors are coupled. The MIF inhibitors can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxide-polylysine substituted with palmitoyl residues. Furthermore, the MIF inhibitors can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, MIF inhibitors are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 80%, from about 5% to about 60%, or from about 1% to about 20% of the MIF inhibitor by weight or volume.

The dosage regimen utilizing the MIF inhibitor is selected in accordance with a variety of factors including type, species, age, weight, sex, race, diet, and medical condition of the patient; the severity of the condition to be treated; the route of administration; the renal or hepatic function of the patient; and the particular MIF inhibitor employed. A physician or veterinarian of ordinary skill in the art can readily determine and prescribe the effective amount of the drug required to prevent, counter or arrest the progress of the condition.

Effective dosage amounts of the present invention, when used for the indicated effects, range from about 0.1 mg to about 5000 mg of the active ingredient per unit dose which could be administered. In one embodiment, the compositions are in the form of a tablet that can be scored. Appropriate dosages of the MIF inhibitors can be determined as set forth in Goodman, L. S.; Gilman, A. The Pharmacological Basis of Therapeutics, 5th ed.; MacMillan: New York, 1975, pp. 201-226, the contents of which are hereby incorporated by reference.

MIF inhibitors can be administered in a single daily dose, or the total daily dosage can be administered in divided doses of two, three or four times daily. Furthermore, MIF inhibitors can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of the MIF inhibitor ranges from about 0.1% to about 15%, w/w or w/v.

The MIF inhibitors can also each be administered in amounts that are sufficient to treat or prevent MIF-associated diseases. These diseases include, but are not limited to, cardiovascular and cerebrovascular diseases, autoimmune diseases, inflammatory disorders, fibrotic diseases, metabolic disorders, and oncologic diseases either individually or in combination with one or more agents and or methods for treating and preventing these MIF-associated diseases.

Compounds according to the present invention may be administered in combination with the following non-limiting examples of therapeutic agents and methods for treating and preventing these MIF-associated diseases in any combination that may include, but are not limited to any of the following: glucocorticoids, nonsteroidal antiinflammatory drugs (NSAIDs) (non-limiting examples include acetominophen, aspirin, capsaicin, diclofenac, diclofenac/misoprostol, efenamic acid, etodolac, felbinac, fenoprofen, flurbiprofen, ketoprofen, ibuprofen, indomethacin, ketorolac, loxoprofen, meclofenamate, meloxicam, nabumetone, naproxen, nimesulide, oxaprozin, piroxicam, sulindac, tolmetin), cyclooxygenase (COX)-2 inhibitors (non-limiting examples include celecoxib, valdecoxib, etoricoxib, lumiracoxib, parecoxib), licofelone (ML3000), disease-modifying antirheumatic drugs (DMARDs), methotrexate, chloroquine, hydroxychloroquine, cyclophosphamide (Cytoxan), inosine monophosphate dehydrogenase (IMPDH) inhibitors (a non-limiting example is mycophenolate mofetil [Cellcept, Myfortic]), sirolimus, everolimus (rapamycin), purine nucleoside phosphorylase inhibitors, de novo purine synthesis inhibitors (non-limiting examples include polygentamate derivatives of methotrexate, antifolate compounds), dihydroorotate dehydrogenase inhibitors (malononitrilamides), prostaglandins PGE2 inhibitors, P2X7 receptor inhibitors, proteinase-activated receptor 2 (PAR-2) inhibitors, inhibitors of activated Complement (non-limiting examples include Eculizumab, Pexelizumab), complement C3/C5 convertase inhibitors (a non-limiting example is Nafamostat mesilate), active convertase inhibitors, complement C5aR antagonists, EP4 agonists, prostaglandin-I2 analogs (non-limiting examples include iloprost, cicaprost, treprostinil), Sulphasalazine (SASP), 5-aminosalicylic acid (5-ASA), immunomodulator drugs (non-limiting examples include azathioprine (AZA), 6-mercaptopurine (6-MP), methotrexate (MTX)), calcineurin inhibitors (non-limiting examples include cyclosporine, voclosporine, tacrolimus), interleukin-10 (AG011), placenta-derived cells (PDA001), mucosal addressin cell adhesion molecule (MAdCAM) inhibitors (PF-00547659), GLP-2 agonists (non-limiting examples include ZP1848, ALX-0600), anti-CD3, CCR9 inhibitors, lenalidomide (Revlimid), recombinant human interleukin-11, CXCR2Antagonists (a non-limiting example is SB-656933), glucagon-like peptide-2 (GLP-2) analogue (Teduglutide), insulin-like growth factor-1 (IGF-1) (Increlex), synthetic guanylhydrazone semapimod (CPSI-2364), intracellular adhesion molecule-1 (ICAM-1) inhibitor (alicaforsen), stem cell therapeutics (a non-limiting example is Prochymal), activated protein C (aPC), vitamin D analogs (a non-limiting example is calcipotriene), retinoids (a non-limiting example is tazarotene), phototherapy (non-limiting examples include broadband ultraviolet B light, narrow band ultraviolet B light, psoralen plus ultraviolet A light), methotrexate, cyclosporine, acitretin, CCR6 inhibitors, CCL20 inhibitors, deoxyspergualin, alkylate deoxyribonucleic acid (DNA) agents, tumor necrosis factor (TNF)-alpha inhibitors (non-limiting examples include etanercept, infliximab, adalimumab, certolizumab pegol (Cimzia), golimumab (CNTO-148)), inhibitors of TNF-alpha converting enzyme, Janus kinase (JAK) 1, 2 and/or 3 inhibitors (non-limiting examples include Tofacitinib, INCB-28050, Ruxolitinib), spleen tyrosine kinase (SYK) inhibitors (a non-limiting example is R-788), caspase inhibitor, chemokine receptor antagonists, protein kinase C (pkc) inhibitors (a non-limiting example is Enzastaurin), p38 mitogen-activated protein kinase (MAPK) inhibitors, caspase inhibitors, NF-κB modulators, B cell inhibitors, Hydroxychloroquine, B-lymphocyte stimulator (BLyS) inhibitors (a non-limiting example is belimumab (Benlysta)), membrane-bound and soluble B-cell activating factor inhibitors (a non-limiting example is LY2127399), inhibitors that antagonize the binding of BLyS and APRIL (a proliferation-inducing ligand) cytokines to B cells in order to prevent B-cell maturation and autoantibody production (a non-limiting example is Atacicept), anti-CD19, CD20 inhibitors (non-limiting examples include Rituximab, Ocrelizumab, Ofatumumab), CD22 inhibitors (a non-limiting example is Epratuzumab), T cell inhibitors (non-limiting examples include Alefacept (Amevive), IPP-201101), interferon inhibitors (non-limiting examples include MEDI-545, rontalizumab, fontalizumab), toll-like receptor inhibitors, prasterone, estrogen receptor antagonist (fulvestrant), cytotoxic T-lymphocyte-associated antigen 4 (CTLA-4)-Ig (a non-limiting example is Abatacept (Orencia)), v-set domain containing T cell activation inhibitor 1 (VTCN1; B7-H4) agonists (AMP-110), interleukin-1 receptor antagonists (AMG 108, Anakinra [Kineret]), interleukin-1 beta antagonists (non-limiting examples include canakinumab, Xoma 052), soluble IL-1 receptors (a non-limiting example is rilonacept), interleukin-2R antagonists (non-limiting examples include basiliximab (Simulect), daclizumab (Zenapax)), interleukin-6 receptor antagonists (non-limiting examples include Tocilizumab [Actemra]), calcipotriene/betamethasone (Taclonex), fumarate (Panaclar/BG-12), interleukin-15 inhibitors, interleukin-17 inhibitors (AIN457), DHODH inhibitors (Vidofludimus), interleukin-18 inhibitors, T helper (Th) 17 cell inhibitors, interleukin 12/interleukin 23 inhibitors (non-limiting examples include Ustekinumab [CNTO-1275], briakinumab [ABT-874]), interleukin-22 inhibitors, interleukin-23 inhibitors, interleukin-12 inhibitors, alpha interferons, beta interferons [Interferon beta-1a (Avonex, Rebif), Interferon beta-1b (Betaseron/Betaferon), Glatiramer acetate (Copaxone), selective adhesion molecule inhibitors, integrin antagonists (Natalizumab [Tysabri], vedolizumab), sphingosine 1-phosphate receptor (S1P-R) agonists (a non-limiting example is Fingolimod [FTY720]), fumarate derivative immunomodulators (a non-limiting example is BG-12), laquinimod, anti-LFA-1 (a non-limiting example is Efalizumab [Raptiva]), MBP-8298, cladribin (a non-limiting example is Mylinax), Novantrone, isoxanol dihydroorotate dehydrogenase (DHODH) and tyrosine kinase inhibitor (a non-limiting example is teriflunomide [HMR-1726]), Revimmune (cyclophosphamide), Fampridine SR (4-aminopyridine), Panaclar (dimethylfumarate), MBP8298 (dirucotide, synthetic peptide version of a portion of human myelin basic protein), Campath (alemtuzumab), anti-CD52, Cladribine, purine analogs, Fingolimod (sphingosine 1-phosphate receptor agonists), Laquinimod, Teriflunomide, de novo pyrimidine synthesis inhibitors (non-limiting examples include brequinar, leflunomide [Arava]), active metabolites of leflunomide, photodynamic therapy [PDT] with verteporfin, Anti-angiogenic factors non-limiting examples include vascular endothelial growth factor A (VEGFA) inhibitors (non-limiting examples include pegaptanib sodium, ranibizumab, bevacizumab), CCR3 inhibitors, anti-CD48, beta 2-agonists, leukotriene modifiers, phosphodiesterase (PDE) inhibitors (non-limiting examples include tetomilast, ibudilast), selective phosphodiesterase-4 (PDE-4) inhibitors (non-limiting examples include rolipram, roflumilast, piclamilast, pentoxifylline), inhibitors targeting IgE (Omalizumab), Th2 cytokine inhibitors (non-limiting examples include suplatast tosilate, sIL-4R, IL-5 inhibitors), Macrolides, Ketolide, adenosine A2B antagonists, kappa B kinase 2 inhibitors, prostanoid and F2-isoprostane antagonists, Nitric oxide donors, inducible nitric oxide synthase inhibitors, toll-like receptor modulators, Lorcaserin, phentermine, topiramate, bupropion, naltrexone, Anti-CD3, Antithymocyte globulin, serine protease inhibitors (a non-limiting example is alpha-1 antitrypsin AAT), tyrosine kinase inhibitors, platelet-derived growth factor receptor (PDGFR) inhibitors, insulin, Antigen-Specific Tolerance inducting agents to Type 1 Diabetes (non-limiting examples include Glutamate Decarboxylase 65 and Heat Shock Protein treatments), cannabinoid receptor 1 (CB1) antagonists, long-acting glucagon-like peptide 1 (GLP1) analogues, dipeptidyl peptidase 4 (DPP4) inhibitors, vasoactive intestinal peptide-pituitary adenylate cyclase-activating polypeptide receptor 2 (VPAC2) agonists, Glucokinase activators, Glucagon receptor antagonists, Cytosolic phosphoenolpyruvate carboxykinase (PEPCK) inhibitors, sodium-glucose co-transporter 2 (SGLT2) inhibitors, salsalate, IκB kinase-β (IKKβ)-inhibitors, nuclear factor kappa B inhibitors, interleukin-1 (IL-1) receptor antagonists, IL-1 beta-specific antibody, sirtuin 1 (SIRT1) activators, selective peroxisome proliferator-activated receptor (PPAR) modulators (SPPARMs), 11β-hydroxysteroid dehydrogenase type 1 (11βHSD1) inhibitors, PPARγ ligands (non-limiting examples include rosiglitazone, pioglitazone, troglitazone), thiazolidinediones, glitazones, Warfarin, coumadin, pradaxa (non-limiting examples include dabigatran etexilate mesylate), anti-thrombotics, Statins, hydroxy-methylglutaryl-coenzyme A reductase (HMG-CoA reductase) inhibitors, ezetimibe, fenofibrates, niacin, amlodipine, Vascular cell-adhesion molecule (VCAM) antagonists, Thromboxane A2 antagonists, prostaglandin D2 receptor 1 antagonists, G-protein-coupled receptor (GPCR) modulators, cannabinoid receptor 1 (also known as CNR1) CB1 receptor antagonists (Rimonabant), cholesteryl ester transfer protein (CETP) inhibitors (JTT-705), chemokine (C—C motif) receptor 2 (CCR2) antagonists, Phospholipase A2 inhibitors, peroxisome proliferator-activated receptor (PPAR) agonists, RNA polymerase inhibitors, Leukotriene synthesis inhibitors, α7 nicotinic receptors (α7 nAChRs) agonists, donepezil, galantamine, rivastigmine, memantine, α-secretase cleavage stimulants, γ-secretase activity inhibitors, antioxidant therapy, estrogens, NO synthetase inhibitors, anti-β-amyloid (Aβ) (bapineuzumab), Abiraterone, ActRIIA signaling inhibitors (ACE-011), adriamycin, aldesleukin [Proleukin], alemtuzumab, alitretinoin, alkylating agents and microtubule inhibitors (non-limiting examples include Taxol, Temozolomide [Temodar]), allopurinol, allosteric Akt inhibitors (Akti) [MK-2206], altretamine, amifostine, anastrozole (Arimidex), triple angiokinase inhibitor that inhibits VEGF receptors (VEGFR) 1, 2, and 3, fibroblast growth factor receptors, and platelet-derived growth factor receptors (BIBF 1120), angiopoietin ½-neutralizing peptibody (AMG 386), anthracycline (amrubicin), antigen-specific cancer immunotherapeutics (ASCI) (non-limiting examples include MAGE-A3, WT1), antimetabolites (Raltitrexed), Apaziquone (EOquin), aprepitant, aromatase inhibitors (non-limiting examples include letrozole [Femara], aromasin), arsenic trioxide, Asparaginase, anaplastic lymphoma kinase (ALK) inhibitor (crizotinib, AP26113), azacitidine (Vidaza), BCG Live, Bcl-2 family inhibitors (a on-limiting example is ABT-263), Bcr-Abl inhibitors (non-limiting examples include nilotinib [Tasigna], AP24534), bendamustine, bexarotene capsules, bexarotene gel, bleomycin, BRAF signaling inhibitors (a non-limiting example is RG7204), busulfan intravenous, busulfan oral, Cabazitaxel (Jevtana), calusterone, capecitabine (Xeloda), carboplatin, carmustine, carmustine with Polifeprosan 20 Implant, caspase inhibitors, anti-CD23, anti-CD30, anti-CD32, anti-CD33, anti-CD40, chlorambucil, cisplatin, cladribine, c-Met receptor tyrosine kinase inhibitors (ARQ197), clofarabine (Clolar), CS 1 inhibitors (a non-limiting example is Elotuzumab), cytotoxic T-lymphocyte-associated antigen 4 (CTLA-4) inhibitors (a non-limiting example is ipilimumab), cyclophosphamide, cytarabine, cytarabine liposomal, dacarbazine, dactinomycin, actinomycin D, Darbepoetin alfa (Aranesp), daunorubicin liposomal, daunorubicin, daunomycin, histone deacetylase (HDAC) inhibitors (non-limiting examples include Istodax, LBH589, Belinostat), decitabine (Dacogen), Delta-like 4 ligand (DLL4) inhibitors (OMP-21M18), Denileukin, diftitox, dexrazoxane, docetaxel (Taxotere), doxorubicin, doxorubicin liposomal, Dromostanolone propionate, DR5 agonists (LBY135), Elliott's B Solution, epidermal growth factor receptor (EGFR) inhibitors (non-limiting examples include Cetuximab [Erbitux], GA201, panitumumab [Vectibix]), epidermal growth factor receptor tyrosine kinase (EGFR-TK) inhibitors (a non-limiting example is gefitinib [Iressa]), EGFR inhibitor-protein-tyrosine kinase inhibitors (a non-limiting example is Erlotinib [Tarceva]), dual EGFR/HER2 receptor tyrosine kinase inhibitors (a non-limiting example is Tovok [BIBW-2992]), elsamitrucin, endothelin-B receptor agonists (a non-limiting example is SPI-1620), epirubicin, Epoetin alfa and beta (non-limiting examples include Procrit, Epogen, NeoRecormon), etoposide phosphate, etoposide (VP-16), exemestane, farnesyltransferase inhibitor (FTI) (a non-limiting example is lonafarnib), fentanyl (non-limiting examples include Fentora, Actiq), floxuridine (intraarterial), fludarabine (non-limiting examples include Fludara, Oforta), fluorouracil (5-FU), fulvestrant (Faslodex), G2 checkpoint abrogator (CBP501), GA101, gemcitabine (Gemzar), gemtuzumab ozogamicin, Gonadotropin-Releasing Hormone (GnRH) agonists (a non-limiting example is goserelin [Zoladex]), goserelin acetate, Granulocyte-Colony Stimulating Factor (non-limiting examples include Filgrastim, Pegfilgastrim), granulocyte macrophage-colony stimulating factor (GM-CSF) (Sargramostim), heat shock protein 90 (Hsp90) inhibitors, hedgehog pathway inhibitor (RG3616), Pan-HER inhibitors (PF-00299804), Herceptin, HPV vaccines (non-limiting examples include Gardasil, Cervarix), human death receptor 5 agonists (a non-limiting example is Conatumumab [AMG 655]), hydroxyurea, Ibritumomab (Zevalin), idarubicin, ifosfamide, imatinib mesylate (Gleevec/Glivec), immunomodulatory drugs (IMiDs) (non-limiting examples include Pomalidomide, Thalidomide, lenalidomide), type 1 insulin-like growth factor receptor (IGF-1R) inhibitors (non-limiting examples include figitumumab, AMG-479, Cixutumumab, dalotuzumab), dual kinase inhibitor of both insulin-like growth factor-1 receptor (IGF-1R) and insulin receptor (IR) (OSI-906), interleukin-2, ipilimumab, irinotecan, Istodax (romidepsin), lapatinib (Tykerb), leteprinim, leucovorin, levamisole, levoleucovorin, LOddC, lomustine (CCNU), leuprorelin, leutinizing hormone releasing hormone (LHRH) agonists (non-limiting examples include Goserelin, leuprolide, Bicalutamide [Casodex]) and antagonists (a non-limiting example is Ozarelix), lucanthone, MAGE-A3-inhibitors (non-limiting examples include GSK-1572932A, GSK-2132231A), MAPK/ERK kinase 1/2 inhibitors (AZD6244), meclorethamine (nitrogen mustard), megestrol acetate, melphalan (L-PAM), mercaptopurine (6-MP), mesna, MET inhibitors (XL184), methotrexate, methoxsalen, midostaurin (PKC412), mifamurtide (Mepact), mitomycin C, mitotane, mitoxantrone, mammalian target of rapamycin (mTOR) inhibitors (non-limiting examples include temsirolimus, ridaforolimus, everolimus [Afinitor]), MEK inhibitors (a non-limiting example is GDC-0973/RG7420), microtubule inhibitors (non-limiting examples include ixabepilone [Ixempra]), Microtubule stabilizers (patupilone [EP0906]), multikinase inhibitors (non-limiting examples include sorafenib [Nexavar], Nelarabine, pazopanib [Votrient]), multitargeted receptor tyrosine kinase inhibitors (TKI) (TKI258), nandrolone phenpropionate, Necitumumab, Neulasta, NK-1 receptor inhibitors, Nofetumomab, Noscapine (CB3304), ondansetron, Oprelvekin, oxaliplatin (Eloxatin), PI3K inhibitors (non-limiting examples include GDC-0941/RG7321, BKM120 and BYL719), Dual PI3K/mTOR Inhibitors (BEZ235), paclitaxel (Abraxane), pamidronate, platelet-derived growth factor receptor alpha (PDGFR-α) inhibitors (IMC-3G3), pegademase, Pegaspargase, Pegfilgrastim, pentostatin, pertuzumab, pipobroman, plicamycin, polo-like kinase 1 (Plk-1) inhibitors, mithramycin, poly (ADP-ribose) polymerase-1 (PARP1) inhibitors (non-limiting examples include MK-4827, Iniparib [BSI-201]), porfimer sodium, integrins avβ3 and avβ5 inhibitors (cilengitide [EMD121974]), Pemetrexed (Alimta), pralatrexate injection (Folotyn), plerixafor (a non-limiting example is Mozobil), dual pro-apoptotic receptor (PARA) DR4 and DR5 agonists (a non-limiting example is recombinant human Apo2L/TRAIL [Dulanermin]), procarbazine, protein-tyrosine kinase inhibitors (a non-limiting example is dasatinib), proteasome inhibitors (a non-limiting example is Bortezomib [Velcade]), quinacrine, raf and VEGFR inhibitors (a non-limiting example is RAF265), Receptor activator of nuclear factor-κB (RANKL) inhibitors (a non-limiting example is denosumab), Rasburicase, multi-targeted receptor tyrosine kinase (RTK) inhibitor (a non-limiting example is sunitinib [Sutent]), romidepsin (Istodax), Seocalcitol (CB1089), polyethyleneglycol-SN38 conjugates (EZN-2208), Satraplatin, dual Src and Bcr-Abl kinase inhibitors (a non-limiting example is bosutinib), streptozocin, talbuvidine (LDT), talc, tamoxifen (Nolvadex), T-DM1, temozolomide, teniposide (VM-26), testolactone, therapeutic vaccines (BiovaxID, IRX-2, Rindopepimut (CDX-110), sipuleucel-T [Provenge], TVA immunotherapy, Stimuvax [BLP25 liposome vaccine]), somatostatin analogues (a non-limiting example is pasireotide [SOM230]), taxane (Ortataxel), tasisulam, thalidomide [Thalomid], thioguanine (6-TG), thiotepa, topoisomerase I and II inhibitors, topoisomerase I inhibitors (gimatecan [LBQ707], irinotecan), topotecan (Hycamtin), toremifene, Trabectedin (Yondelis), Trastuzumab, tretinoin (ATRA), Tositumomab (Bexxar), TRPM8 agonists (D-3263), uracil mustard, recombinant urate-oxidase (Elitek), valrubicin, valtorcitabine (monoval LDC), antagonists of vascular endothelial growth factor receptors 1, 2 and 3 ("VEGFR1-3")/platelet-derived growth factor receptor ("PDGFR")/stem cell factor receptor ("c-kit") (motesanib), vascular endothelial growth factor receptor (VEGFR)/epidermal growth factor receptor (EGFR)/rearranged during transfection (RET) tyrosine kinase inhibitors (vandetanib), vascular endothelial growth factor (VEGF) inhibitors (Cediranib, Ramucirumab), VEGFR/EGFR/HER-2 inhibitors (AEE788), vinblastine, vinorelbine, Wnt signaling inhibitors (OMP-18R5), zoledronate, zoledronic acid and combinations thereof, among others.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Compounds

The following non-limiting compound examples serve to illustrate further embodiments of the MIF inhibitors. It is to be understood that any embodiments listed in the Examples section are embodiments of the MIF inhibitors and, as such, are suitable for use in the methods and compositions described above.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

Example 1

Synthesis of 1-methyl-2-oxo-4-[4-(thiophen-2-ylcarbonyl)piperidin-1-yl]-1,2-dihydroquinoline-3-carbonitrile, Compound IV

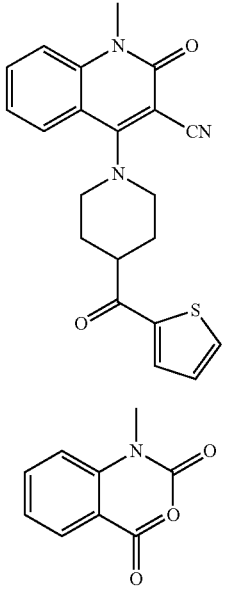

Step 1: Synthesis of 1-methyl-2H-3,1-benzoxazine-2,4(1H)-dione; Compound I

Commercially available 2H-3,1-benzoxazine-2,4(1H)-dione (61.3 mmol, 1.0 eq)) was taken up in N,N-dimethylformamide (120 ml) then treated with portion wise addition of sodium hydride (60% oil dispersion, 67.4 mmol, 1.1 eq). After stirring 30 minutes, methyl iodide (64.4 mmol, 1.05 ml) was dripped in over 5 minutes. The reaction stiffed at room temperature for 15 h. To quench, a mixture of saturated NH$_4$Cl:H20 (1:1, 100 ml) was added. After stirring for 30 minutes, a solid formed that was collected by vacuum filtration and dried to afford 6.5 g (60% yield) of compound I as a yellow solid. $^1$H-NMR (DMSO-d$_6$): δ 8.1-8.0 (m, 1H), 7.9-7.8 (m 1H), 7.5 (d, J=8.7 Hz, 1H), 7.4-7.3 (m, 1H), 3.5 (s, 3H); LC/MS m/z calc M+H 178, obs M+H 178.

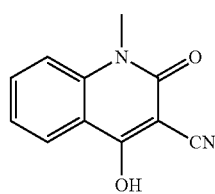

Step 2: Synthesis of 4-hydroxy-1-methyl-2-oxo-1,2-dihydroquinoline-3-carbonitrile; Compound II Compound I, (2.50 g, 14.1 mmol) was dissolved in N,N-dimethylformamide (30 ml) the treated with ethylcyano acetate (1.58 ml, 14.8 mmol) followed by portion wise addition of sodium hydride (60% oil dispersion, 16.9 mmol, 2.2 eq). The reaction stirred 15 hours at room temperature and was then quenched by the addition of 10% HClaq (15 ml). The mixture stirred 30 minutes resulting in a yellow solid which was filtered, washed with water, and dried to afford 1.75 g (62%) of compound II. $^1$H-NMR (DMSO-d$_6$): δ 8.1 (d, J=8.1 Hz, 1H), 7.6 (t, J=7.2, 1H), 7.5 (d, J=8.1 Hz, 1H), 7.2 (t, J=7.8 Hz, 1H), 3.6 (s, 3H); LC/MS m/z calc M+H 200, obs M+H 201.

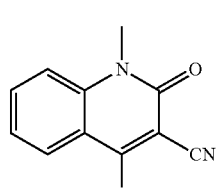

Step 3: Synthesis of 4-chloro-1-methyl-2-oxo-1,2-dihydroquinoline-3-carbonitrile; Compound III Compound II (1.13 g, 5.64 mmol) was taken up in N,N-dimethylacetamide (10 ml). The solution was then treated with lithium chloride (1.20 g, 5.0 eq) and p-toluenesulfonyl chloride (1.29 g, 1.20 eq). The mixture stirred at room temperature for 1 h and was then quenched with 10% HCl aq. (10 ml). After stirring for 30 minutes, a solid formed which was collected by vacuum filtration, washed with water (2×), and dried for product, compound III as a white solid (1.12 g, 91% yield; calc M+H 219, obs M+H 219).

Step 4: Synthesis of 1-methyl-2-oxo-4-[4-(thiophen-2-ylcarbonyl)piperidin-1-yl]-1,2-dihydroquinoline-3-carbonitrile, Compound IV The title compound was prepared as follows. A round bottom flask equipped with heating mantel and water condenser was charged with Compound III (75 mg, 0.34 mmol) along with commercially available piperidin-4-yl(thiophen-2-yl)methanone (Ryan Scientfic, 70 mg, 0.36 mmol), triethylamine (0.040 ml, 1.0 eq) and toluene (3 ml). The reaction was heated at reflux for 8 hours. The reaction was concentrated to residue then recrystallized from warm ethylacetate to afford 0.11 g (86% yield) of the title compound IV as a tan solid. $^1$H-NMR (DMSO-d$_6$): δ 8.2-8.0 (m, 2H), 7.9-7.7 (m, 2H), 7.6 (m, 1H), 7.4-7.2 (m, 2H), 3.8-3.5 (m, 5H), 3.3 (s, 3H), 2.1-1.8 (m, 4H); LC/MS calc M+H 378, obs M+H 378.

Example 2

Synthesis of 1-methyl-2-oxo-4-[4-(thiophen-2-ylcarbonyl)azetidin-3-yl]-1,2-dihydroquinoline-3-carbonitrile; Compound V

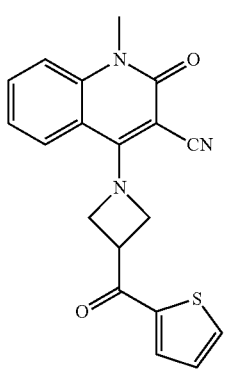

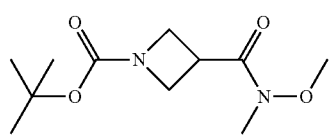

Step 1: Synthesis of tert-butyl 3-[methoxy(methyl)carbamoyl]azetidine-1-carboxylate, Compound VI Commercially available 1-(tert-butoxycarbonyl)azetidine-3-carboxylic acid (0.50 g, 1.0 eq) was dissolved in tetrahyrdofuran (5 ml) then treated with carbonyl diimidazole (0.48 g, 1.2 eq) and diisopropylethylamine (0.95 ml, 2.2 eq). The reaction stiffed for 30 minutes at room temperature then the weinrib amine (0.27 g, 1.1 eq) was added. The reaction continued for 15 hours at room temperature. The reaction was worked up by diluting with saturated NH$_4$Cl aq. (5 ml) then extracted with ethylacetate (2×-10 ml). The organics were pooled and washed with water (2×-10 mL) then brine (1×-10 mL). The organics were dried over Na$_2$SO$_4$ and concentrated to give 0.60 g of compound VI (98% yield). $^1$H-NMR (DMSO-d$_6$): δ 4.0-3.8 (m, 4H), 3.8-3.7 (m, 1H), 3.6 (s, 3H), 3.1 (s, 3H); LC/MS m/z calc M+Na 267, obs M+Na 267.

VII

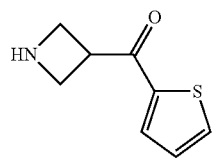

Step 2: Synthesis of azetidin-3-yl(thiophen-2-yl)methanone, Compound VII

Compound VI (0.60 g, 1.0 eq) was taken up in tetrahydrofuran (6 ml) then cooled to 0 dC. A solution of commercially available thiophen-2-yl-magnesium bromide (1.0 M, 2.95 ml, 1.2 eq) was dripped in over 5 minutes. The reaction was allowed to warm to room temperature while stirring over 2 hours. Reaction was diluted with saturated NH$_4$Cl aq. then extracted with ethyl acetate (2×-10 ml). The organics were pooled and washed with water (2×-10 mL) then brine (1×-10 mL). The organics were dried over Na$_2$SO$_4$ and concentrated for crude oil that was purified via silica gel eluting with 0-75% ethylacetate:hexanes to afford the intermediate as a clear oil. Half of the oil was taken up in dioxane (3 ml) and treated with 4 N HCl in dioxane (3 ml). After stirring for 15 hours at room temperature, the reaction was concentrated to oily residue (0.16 g, 89% over 2 steps, calc M+H 168, obs M+H 168).

Step 3: Synthesis of 1-methyl-2-oxo-4-[4-(thiophen-2-ylcarbonyl)azetidin-3-yl]-1,2-dihydroquinoline-3-carbonitrile; Compound V The title compound was prepared as outlined in step 4 of protocol 1.

$^1$H-NMR (DMSO-d$_6$): δ 8.1 (m, 1H), 8.0-7.8 (m, 2H), 7.7 (m, 1H), 7.5 (m, 1H), 7.4-7.2 (m, 2H), 5.1 (t, J=8.0 Hz, 2H), 4.9 (m, 2H), 4.5 (m, 1H), 3.5 (s, 3H); LC/MS Calc M+H 350; obs M+H 350.

Example 3

Synthesis of Compound VIII N-[1-(3-cyano-1-methyl-2-oxo-1,2-dihydroquinolin-4-yl)piperidin-4-yl]thiophene-2-carboxamide

VIII

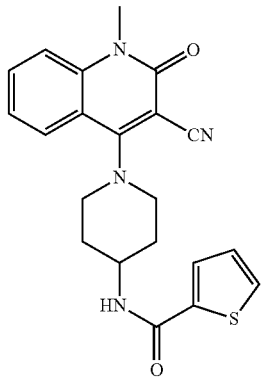

IX

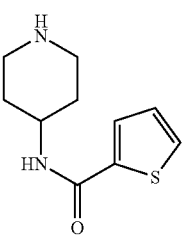

Step 1: Synthesis of N-(piperidin-4-yl)thiophene-2-carboxamide, Compound IX

Commercially available tert-butyl 4-aminopiperidine-1-carboxylate (0.50 g, 1.0 eq) was taken up in dichloromethane and treated with triethylamine (0.42 mL, 1.2 eq). After stirring for 5 minutes, thiophene-2-carbonyl chloride (0.29 ml, 1.1 eq) was slowly added. The reaction stiffed for 15 hours at room temperature. To work up, dichloromethane (5 mL) was added. The organics were washed with water (3×-5 mL) then dried over Na$_2$SO$_4$ and concentrated for 0.80 g tan oil (obs M+Na 323, calc M+Na 323). This product was dissolved in dioxane (5 mL) and treated with 4 N HCl in dioxane (1.88 ml). After stiffing for 15 hours at room temperature, the reaction was concentrated to oily residue (0.63 g, 100% over 2 steps, calc M+H 211, obs M+H 211).

Step 2: Synthesis of Compound VIII N-[1-(3-cyano-1-methyl-2-oxo-1,2-dihydroquinolin-4-yl)piperidin-4-yl]thiophene-2-carboxamide The title compound was prepared as described above in example 1, step 4. $^1$H-NMR (DMSO-d$_6$): δ 8.4 (d, J=8.1 Hz, 1H), 7.9-7.7 (m, 3H), 7.6 (d, J=8.7 Hz, 1H), 7.3 (t, J=8.1 Hz, 1H), 7.2-7.1 (m, 1H), 4.1 (m, 1H), 3.9-3.7 (m, 2H), 3.6-3.3 (m, 5H), 2.1-1.7 (m, 4H); LC/MS (calc M+H 393; obs 393)

Example 4

Synthesis of 1-(3-cyano-1-methyl-2-oxo-1,2-dihydroquinolin-4-yl)piperidine-4-carboxylic acid, Compound X

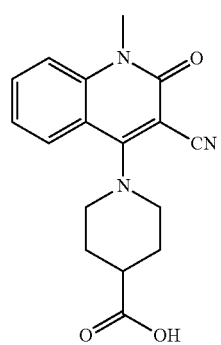

X

Compound III (0.10 g, 1.0 eq) was taken up in 1,4-dioxane (4 ml) and treated with pyridine (43 uL, 1.10 eq) and methyl isonipecotate (72 mg, 1.1 eq). The mixture was heated at 85° C. for 15 hours. The reaction was dried down to a gummy solid via N₂ stream. This residue was taken up in ethylacetate (5 mL). The organic was washed with 10% HCl aq. (2×-3 mL), water (3×-5 mL), and brine (2×-5 mL) then dried over Na₂SO₄ and concentrated for 0.085 g tan gummy solid (obs M+H 326, calc M+H 326). This product was dissolved in tetrahydrofuran (2 mL) and treated with 6 N NaOHaq (0.5 mL). After stirring for 15 hours at room temperature, the reaction was concentrated to white solid residue that was taken up in H₂O (1 mL) and acidified to pH 5 via 10% HClaq. The resulting white solid was collected and dried for 0.081 g of product (56.6% over 2 steps, calc M+H 312, obs M+H 312).

Example 5

Synthesis of 1-(3-cyano-1-methyl-2-oxo-1,2-dihydroquinolin-4-yl)N-(pyridin-4-ylmethyl)piperidine-4-carboxamide, Compound XI

XI

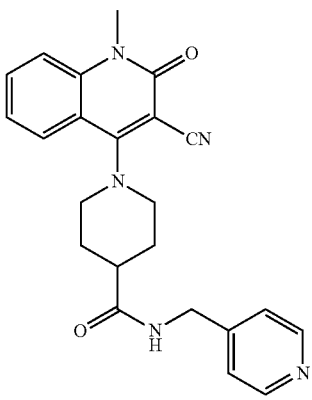

Compound X (0.10 g, 1.0 eq) was taken up in N,N-dimethylacetamide (2 ml) then treated with HBTU (0.16 g, 1.3 eq) and triethylamine (49 uL, 1.1 eq). After 10 minutes at room temperature, commercially available 4-aminomethylpyridine (37.8 mg, 1.1 eq) was added. The reaction stirred at room temperature for 15 h before diluting with saturated NH₄Cl aq. to quench. The mixture was extracted with ethylacetate (3×-5 ml). The organics were washed with water (3×-5 mL), and brine (2×-5 mL) then dried over Na₂SO₄ and concentrated for crude material. The residue was loaded on silica gel (24 g) and eluted with a gradient of 0-10 MeOH/DCM for 20 CVs. Late fractions afforded the desired product as a lightly tan solid (5.1 mg, 3.8% yield; calc M+H 402, obs M+H 402).

Example 6

The following compounds were prepared by amide coupling of compound X with the requisite amines following the procedure set out in Example 5:

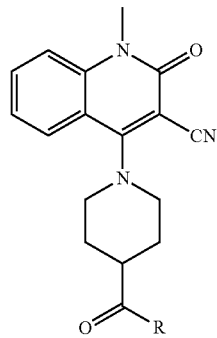

| Compound # | R | M + H |
|---|---|---|
| XII | ⟨-N(CH₃)₂⟩ | 339 |
| XIII | ⟨-NH-CH₂CH₂-OH⟩ | 355 |
| XIV | ⟨H₂N-thiazol-2-yl⟩ | 394 |
| XV | ⟨H₂N-pyrazol-3-yl⟩ | 377 |
| XVI | ⟨H₂N-pyrimidin-2-yl⟩ | 388 |

Example 7

Synthesis of Compound XVII 1-methyl-2-oxo-4-{[1-(thiophen-2-ylcarbonyl)piperidin-4-yl]amino}-1,2-dihydroquinoline-3-carbonitrile

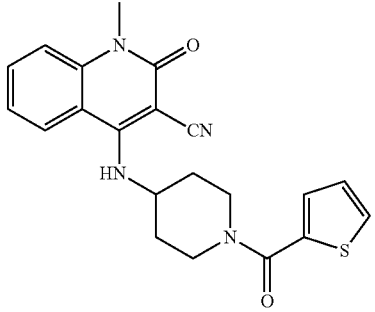

XVII

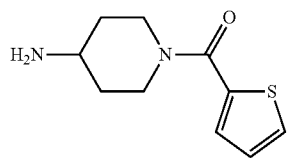

XVIII

Step 1: Preparation of Compound XI (4-aminopiperidin-1-yl)(thiophen-2-yl)methanone, Compound XVIII Commercially available tert-butyl piperidin-4-ylcarbamate (0.50 g, 1.0 eq) was taken up in dichloromethane (2 ml) and treated with triethylamine (0.42 mL, 1.2 eq). Afte stirring for 5 minutes, chloroacyl thiophene (0.29 ml, 1.1 eq) was dripped in slowly. The reaction stirred 15 hours at room temperature before being diluted with DCM (5 ml) and washed with water (3×-5 ml). The organics were dried over $Na_2SO_4$ and concentrated for a tan oil. The oil was taken up in 1,4-dioxane (2 ml) and stiffed with 4N HCl in dioxane (1.88 ml) for 15 hours at room temperature. The solvent was evaporated and the solid was triturated with diethyl ether (3×-5 ml) to afford the HCl salt product as a yellow solid (0.62 g, 100% yield over 2 steps; calc M+H 211, obs M+H 211).

Step 2: 
The title compound was prepared by addition of intermediate III and compound XVIII as outlined in example 1; step 4. $^1$H-NMR (DMSO-$d_6$): δ 8.3 (d, J=7.5 Hz, 1H), 7.8-7.6 (m, 2H), 7.6-7.2 (m, J=8.1 Hz, 1H), 7.2 (t, J=7.8 Hz, 1H), 3.6 (s, 3H); LC/MS Calc M+H, 393; obs 393.

Example 8

Synthesis of Compound XIX 1-(3-cyano-1-methyl-2-oxo-1,2-dihydroquinolin-4-yl)-N-(pyridin-4-ylmethyl)azetidine-3-carboxamide

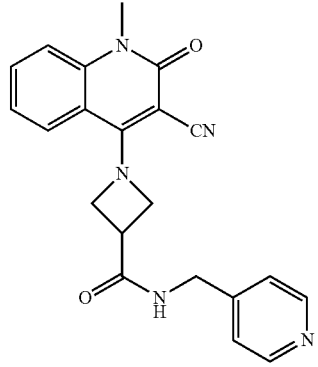

XIX

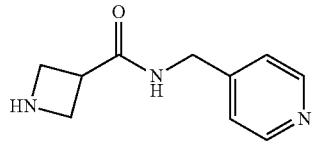

XX

Step 1: Preparation of N-(pyridin-4-ylmethyl)azetidine-3-carboxamide, Compound XX Commercially available 1-(tert-butoxycarbonyl)azetidine-3-carboxylic acid (0.17 g, 1.0 eq) was taken up in N,N-dimethylacetamide (2.5 ml) then treated with HBTU (0.38 g, 1.2 eq) and triethylamine (0.18 ml, 1.5 eq). After 10 minutes at room temperature, commercially available 4-aminomethylpyridine (94 uL, 1.1 eq) was added. The reaction stirred at room temperature for 3 h before diluting with $H_2O$ to quench. The mixture was extracted with ethylacetate (3×-5 ml). The organics were washed with 5% HCl aq. (2×-5 ml), water (3×-5 mL) and brine (2×-5 mL) then dried over $Na_2SO_4$ and concentrated to oily residue. The residue was taken up in 1,4-dioxane (2 ml) and stirred with 4N HCl in dioxane (1.88 ml) for 15 hours at room temperature. The solvent was evaporated and the solid was triturated with diethyl ether (3×-5 ml) to afford the HCl salt product as a gummy solid (0.29 g, 100% yield over 2 steps; calc M+H 192, obs M+H 192).

Step 2: The title compound was prepared by addition of compound XX to compound III as outlined in example 1, step 4. Calc M+H 374, obs 374

Example 9

Synthesis of N-[1-(3-cyano-1-methyl-2-oxo-1,2-dihydroquinolin-4-yl)azetidin-3-yl]thiophene-2-carboxamide, Compound XXI

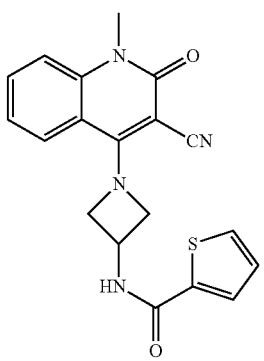

XXI

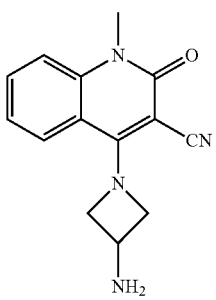

XXII

Step 1: Preparation of 4-(3-aminoazetidin-1-yl)-1-methyl-2-oxo-1,2-dihydroquinoline-3-carbonitrile, Compound XXII Compound III (0.10 g, 1.0 eq) and commercially available tert-butyl azetidin-3-ylcarbamate (83 mg, 1.05 eq) were taken up in N,N-dimethylacetamide (1.5 ml). The mixture was then treated with 60% NaH oil dispersion (22 mg, 1.2 eq). After stirring for 1 h, reaction was quenched with 10% HCl aq. (0.5 ml) then H₂O (1 ml). A solid formed that was collected and dried. Half of this solid was suspended in 1,4 dioxane (3 ml) and treated with 4N HCl in dioxane (1.0 ml). Reaction stirred for 15 h before concentrating to residue and triturating with diethyl ether. Product was obtained as a yellow solid (76 mg 100% yield for two steps, calc M+H 255, obs M+H 255).

Step 2: Preparation of the title compound, N-[1-(3-cyano-1-methyl-2-oxo-1,2-dihydroquinolin-4-yl)azetidin-3-yl] thiophene-2-carboxamide, compound XXI was accomplished as follows.

A round bottom flask equipped with heating mantel and water condenser was charged with compound XXII (81 mg, 1.0 eq) along with commercially available piperidin-4-yl (thiophen-2-yl)methanone (Ryan Scientfic, 56 mg, 1.1 eq), triethylamine (0.044 ml, 1.2 eq) and toluene (3 ml). The reaction was heated at reflux for 8 hours. The reaction was concentrated to residue then recrystallized from acetone/water to afford 0.051 g (42% yield) of the title compound as a tan solid. ¹H-NMR (DMSO-d₆): δ 9.2 (s, 1H), 7.8-7.6 (m, 4H), 7.5 (d, J=8.7, 1H), 7.3-7.1 (m, 2H), 5.2-5.0 (m, 2H), 4.8-4.6 (m, 3H), 3.5 (s, 3H); LC/MS calc M+H 472, obs M+H 472).

Example 10

Synthesis of Compound XXIII, 4-(azetidin-3-ylamino)-1-methyl-2-oxo-1,2-dihydroquinoline-3-carbonitrile

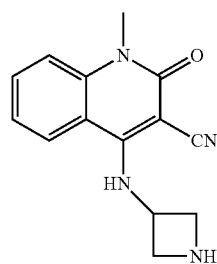

XXIII

The title compound was prepared from compound III and 1-BOC-3-aminoazetidine as outlined in example 9, step 1. Calc M+H 255, obs 255.

Example 11

The following compounds were prepared from the appropriate scaffold and the requisite acid or sulfonyl chloride following the procedure outlined in example 9, step 2:

| Compound | Structure | M + H |
|---|---|---|
| XXIV | 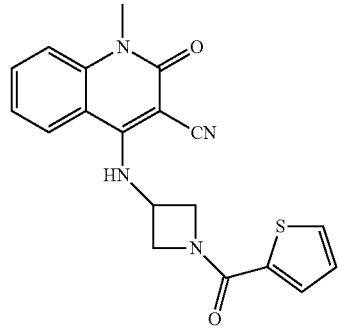 [SMILES: Cn1c(=O)c(C#N)c(NC2CN(C(=O)c3cccs3)C2)c2ccccc21] | 365 |
| XXV | 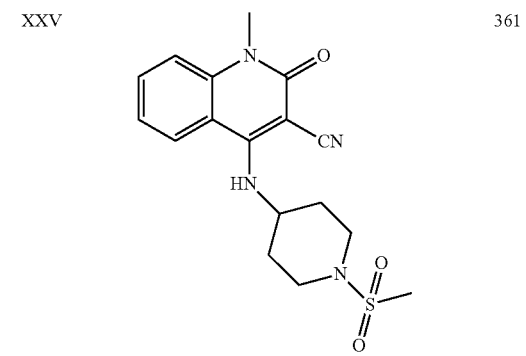 | 361 |

-continued

| Compound | Structure | M + H |
|---|---|---|
| XXVI | 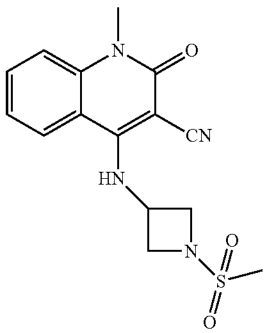 [SMILES: Cn1c(=O)c(C#N)c(NC2CN(S(C)(=O)=O)C2)c2ccccc21] | 333 |
| XXVII | 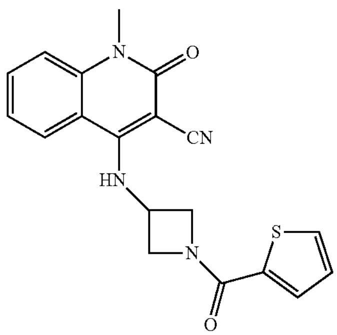 [SMILES: Cn1c(=O)c(C#N)c(NC2CN(C(=O)c3cccs3)C2)c2ccccc21] | 401 |

Example 12

1-(4-fluorobenzyl)-2-oxo-4-[4-(thiophen-2-ylcarbonyl)piperidin-1-yl]-1,2-dihydroquinoline-3-carbonitrile, Compound XXVIII

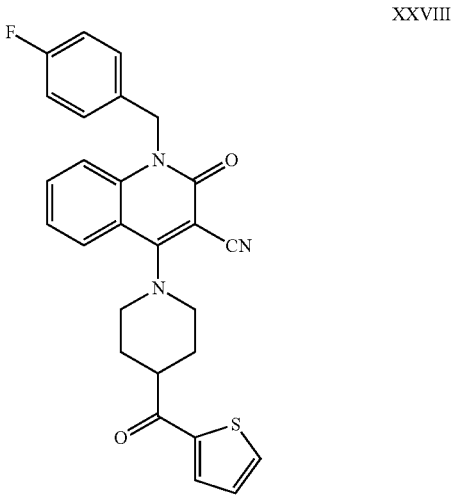

XXVIII

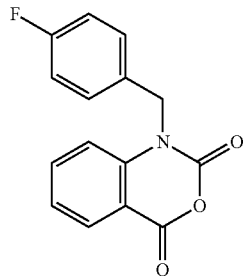

XXIX

Step 1: Synthesis of 1-(4-fluorobenzyl)-2H-3,1-benzoxazine-2,4(1H)-dione, Compound XXIX Commercially available 2H-3,1-benzoxazine-2,4(1H)-dione (1.0 g, 1.0 eq)) was taken up in N,N-dimethylformamide (15 ml) then treated with portion wise addition of sodium hydride (60% oil dispersion, 0.26 g, 1.05 eq). After stirring 30 minutes, p-fluorobenzyl bromide (1.22 g, 1.05 eq) was dripped in over 5 minutes. The reaction stirred at room temperature for 1 hour. A slurry of yellow solid resulted. Water (15 ml) was added to aid filtration. The solid was collected and recrystallized from ethyl acetate and hexanes (1:3) to afford 1.2 g (73%) of a brown crystalline solid. $^1$H-NMR (DMSO-$d_6$): δ 8.0-7.9 (m, 1H), 7.8 (t, J=8.7 Hz, 1H), 7.5 (dd, J=8.7, 5.4 Hz, 2H), 7.3-7.0 (m, 4H), 5.3 (s, 2H); LC/MS calc M+Na 294, obs M+Na 294.

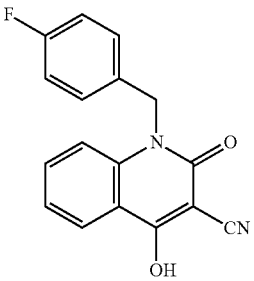

XXXI

Step 2: Synthesis of 1-(4-fluorobenzyl)-4-hydroxy-2-oxo-1,2-dihydroquinoline-3-carbonitrile, compound XXXI. Compound XXX, (18.5 g, 1.0 eq) was dissolved in N,N-dimethylformamide (250 ml) then treated with ethylcyano acetate (7.64 ml, 1.05 eq) followed by portion wise addition of sodium hydride (60% oil dispersion, 6.00 g, 2.2 eq). The reaction stirred 1.5 hours at room temperature and was then quenched by the addition of 10% HCl aq. (150 ml). The mixture stirred 30 minutes resulting in a yellow solid which was filtered, washed with water, and dried to afford 21.2 g (100% yield) of the title compound. $^1$H-NMR (DMSO-$d_6$): δ 7.9 (d, J=7.8 Hz, 1H), 7.3-6.9 (m, 8H), 5.3 (s, 2H); LC/MS m/z calc M+Na 317, obs M+Na 317.

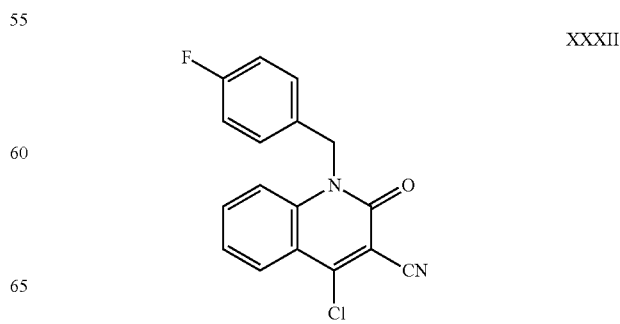

XXXII

Step 3: Synthesis of 4-chloro-1-(4-fluorobenzyl)-2-oxo-1,2-dihydroquinoline-3-carbonitrile, compound XXXII. Compound XXXI (6.00 g, 1.0 eq) was taken up in N,N-dimethylacetamide (50 ml). The solution was then treated with lithium chloride (4.30 g, 5.0 eq) and methanesulfonyl chloride (2.80 g, 1.20 eq). The mixture stiffed at room temperature for 2 h and was then quenched with saturated $NH_4Cl$ aq. (100 ml). After stirring for 30 minutes, a solid formed which was collected by vacuum filtration, washed with water (2×), and dried for product. The desired compound XXXII was obtained as a yellow solid (6.40 g, 100% yield; calc M+Na 335, obs M+Na 335).

Synthesis of the Title 1-(4-fluorobenzyl)-2-oxo-4-[4-(thiophen-2-ylcarbonyl)piperidin-1-yl]-1,2-dihydroquinoline-3-carbonitrile, Compound XXVIII A round bottom flask equipped with heating mantel and water condenser was charged with Compound C (81 mg, 1.0 eq) along with commercially available piperidin-4-yl (thiophen-2-yl)methanone (Ryan Scientfic, 56 mg, 1.1 eq), triethylamine (0.044 ml, 1.2 eq) and toluene (3 ml). The reaction was heated at reflux for 8 hours. The reaction was concentrated to residue then recrystallized from acetone/water to afford product, The title compound was obtained as a tan solid (0.051 g, 42% yield). $^1$H-NMR (DMSO-$d_6$): δ 8.2 (d, J=3.9 Hz, 1H), 8.1 (d, J=4.8 Hz, 1H); 7.8 (d, J=8.1 Hz, 1H), 7.7-7.6 (m, 1H), 7.5-7.2 (m, 5H), 7.2-7.1 (M, 2 H), 5.5, (s, 2H), 3.9-3.7 (m, 3H), 3.6 (t, J=10.4 Hz, 2 H), 2.2-1.8 (m, 4H). LC/MS calc M+H 472, obs M+H 472.

Example 13

The following compounds were prepared as outlined in the above schemes by the procedures detailed in the proceeding examples:

| Compound | Structure | M + H |
|---|---|---|
| XXXIII | (structure) | 487 |
| XXXIV | (structure) | 495 |
| XXXV | (structure) | 454 |
| XXXVI | (structure) | 459 |

-continued

| Compound | Structure | M + H |
|---|---|---|
| XXXVII | 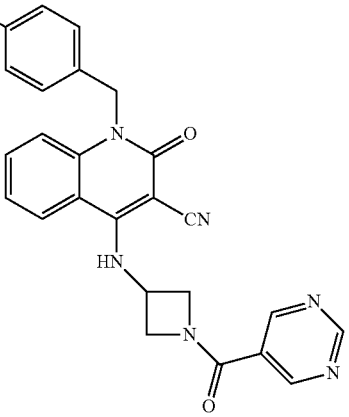 | 455 |
| XXXVIII | 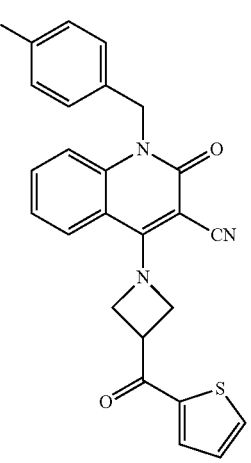 | 444 |

Biological Examples

The methodologies described herein and below are designed to (1) quantitate and describe the nature of the physical interaction between MIF and candidate compounds, (2) determine the biological consequence resulting from the interaction of MIF with the candidate compound and (3) evaluate the impact of the candidate compound in animal models of MIF mediated disease.

Example 14

Tautomerase Activity

Native human MIF exhibits the ability to catalyze a tautomerase reaction, the physiological importance of which remains controversial. The ability of candidate compounds to inhibit this tautomerase activity are quantitated by using hydroxyphenyl pyruvic acid (HPP) as a substrate (Ouertatani-Sakouhi et al., 2010). The ability of compounds to inhibit the tautomerase activity can be quantitated by following the increase in absorbance due to the enzymatic formation of the HPP enol-borate complex at 300 nm in the absence and presence of a test compound. The $IC_{50}$ value of compounds are determined by plotting the initial velocities determined at 300 nm as a function of a test compound's concentration. Assays are carried out in a 96 or 384 well plate format. Representative MIF inhibitors were tested in the assay described above and the results tabulated in Table 1 wherein "A" represents≤10 µM; "B" represents>10 µM and <100 µM; "C" represents>100 µM and ≤200 µM; and "D" represents>200 µM.

TABLE 1

| Compound | Tautomerase IC50 (µM) |
|---|---|
| IV | C |
| XXVIII | C |
| V | B |
| XXXVIII | C |
| X | D |
| XII | D |
| XI | D |
| XIII | D |
| XVII-1 | A |
| VIII | A |
| XXXIII | A |
| XIV | A |
| XV | A |
| XVI | A |
| XIX | A |
| XXIV | A |
| XXI | B |
| XXV | D |
| XXVI | B |
| XXVII | B |
| XXXIV | D |
| XXXV | A |
| XXXVI | A |
| XXXVII | B |

Example 15

Interaction of Candidate Compound with MIF

Direct binding of candidate compounds with MIF is quantitated using surface plasmon resonance (Biacore analysis), a technique that measures bimolecular interactions through refractive index changes on a biospecific chip surface. For these experiments, recombinant human MIF expressed with an amino terminal biotin tag is immobilized on a streptavidin bioactive surface. The candidate compound is passed over the chip surface at various concentrations and binding quantitated in a time and concentration dependent manner. Association (k+1) and dissociation (k-1) rate constants as well as equilibrium dissociation constants (KD) will be generated on each candidate compound.

Example 16

MIF:CD74 Binding Inhibitory Activity

The productive interaction between MIF and its receptors has been demonstrated to be critical for the initiation of biological activity. CD74 represents one of the key receptors for MIF that is expressed on the cell surface of immune cells including macrophages. The interaction between CD74 and MIF is quantitated using surface plasmon resonance (Biacore analysis), a technique that measures bimolecular interactions through refractive index changes on a biospecific chip surface. The extracellular domain of recombinant human CD74 (residues 73-232) expressed with a biotin tag is immobilized on a streptavidin bioactive surface. Recombinant human MIF is passed over the immobilized CD74 at various concentrations and the binding affinity of the CD74:MIF interaction in the absence of compound determined. The ability of compounds to block the MIF:CD74 complex is examined by co-injecting a mixture of MIF and varied concentrations of compound over immobilized CD74. The $IC_{50}$ for compounds will be determined by plotting the decrease in the maximal refractive index in the absence of compound vs. the concentration of compound. Control experiments are carried out to establish that compounds are not binding to CD74 directly.

Example 17

MIF:CXCR2 and CXCR4 Binding Inhibitory Activity

Cold competition radioligand binding studies are utilized to quantitate the MIF:CXCR4 binding inhibitory activity of candidate compounds. The ability of unlabeled human recombinant MIF to compete with $^{125}$I-CXCL12 (the cognate CXCR4 ligand) binding to Jurkat T cells endogenously expressing CXCR4 will be quantitated in a concentration dependent manner and the inhibitory constant for this interaction (Ki) determined Candidate compound modulation of this binding is determined following a 30 minutes preincubation with MIF. The impact of candidate compounds on the potency of MIF competing with tracer CXCL12 binding to CXCR4 on Jurkat cells will be quantitated in a concentration dependent manner using assay conditions that take into account the multiple equilibria present in the reaction. Control experiments will be carried out to establish that candidate compounds are not binding to CXCR4.

A similar approach is used to evaluate the effect of candidate compounds on MIF:CXCR2 binding. In this example, radioligand binding studies quantitating the affinity (Ki) of unlabeled recombinant human MIF to compete with tracer levels of $^{125}$I-CXCL8 (the cognate CXCR2 ligand) for binding to human CXCR2 ectopically expressed on the surface of HEK293 cells will be studied. Candidate compound modulation of this binding is determined following a preincubation with MIF. The impact of candidate compounds on the potency of MIF competing with tracer CXCL8 binding to CXCR2 will be quantitated in a concentration dependent manner using assay conditions that take into account the multiple equilibria present in the reaction.

Example 18

Effect of Candidate Compounds on Cytokine Production from Human Monocytic Monomac 6 Cells Effect of Candidate Compounds on Cytokine Production from Human Cells: Mono-Mac-6 Cells: The cellular efficacy of the inhibitors is determined using the human monocytic cell line, Mono-Mac-6 cells (MM6 cells) as it has been shown that MIF induces the production of inflammatory mediators, including tumor necrosis factor-α (TNF-α) interleukin (IL)-1β, IL-6, IL-8, interferon-γ (IFN-γ) and prostaglandin E2 (PGE2) in these cells (Schwartz et al., 2009). Recombinant human MIF (rhMIF) will be purchased from R&D Systems (Minneapolis, Minn.) or generated in house. To induce the production of inflammatory mediators, MM6 cells will be plated at a final concentration of 5×105 cells/ml in RPMI 1640 medium containing 1% heat-inactivated low-pyrogen fetal bovine serum, 2 mM GlutaMAX-1,1% non-essential amino acids, 1% sodium pyruvate, 100 units/ml penicillin G and 100 µg/ml streptomycin (Gibco BRL Life Technologies). Cells will be stimulated with 100 ng/ml rhMIF with or without inhibitor for 20 h at 37° C. with 5% $CO_2$. The supernatants were stored at −20° C. until they were assayed. The levels of inflammatory mediators will be determined using commercial ELISA kits from R&D Systems (Minneapolis, Minn.). Human Periperal Blood Mononuclear Cells (PBMC): Human whole blood is collected from healthy donors in sodium-heparinized tubes (BD Biosciences), and peripheral blood mononucleated cells (PBMC) are isolated by Ficoll separation. Cells are washed in Dulbecco's phosphate-buffered saline, resuspended in media (DMEM) containing 5% low endotoxin (<0.3 EU/ml) fetal Bovine Serum (FBS, GIBCO) and 10 units/ml penicillin/streptomycin, and plated at 5×105 cells/well in 96-well tissue culture plates. Lipopolysaccharide (LPS, *E. coli* Serotype 0111:B4, Sigma) or macrophage migration inhibitory factor are pre-incubated for 15 minutes with compounds dissolved in dimethyl sulfoxide (DMSO). The mixtures are then added to cells to yield final concentrations of 1% DMSO, 100 ng/ml LPS and 1 µg/ml MIF. Cells are incubated for overnight at 37° C., 5% CO2. TNF-α production is measured by ELISA (R&D Systems). Cytotoxicity is assessed using the MTT [3-(4,5-dimethylthiazol-2-yl)-2,5-diphenyl tetrazolium bromide assay. Human Rheumatoid Arthritis Synovial Fibroblast (RASF) Cell Line: RASF cells are derived from the inflamed synovium of a female RA patient who was undergoing total knee replacement. Cells are cultured in Dulbecco's modified Eagle's medium with 15% FBS, 1% glutamine, and 1% penicillin/streptamycin (all from Gibco (Invitrogen), Gaithersburg, Md.). Experiments are performed with cells between passages 7 to 10, using trypsin with 0.25% ethylene diamine tetraacetic acid (EDTA)(Gibco) to detach cells. Interleukin 1 or macrophage migration inhibitory factor (MIF, GIBCO) are pre-incubated for 15 minutes with compounds dissolved in dimethyl sulfoxide (DMSO). The mixtures are then added to cells to yield final concentrations of 1% DMSO, 1 ng/ml Interleukin 1 or 1 µg/ml MIF. RASFs are incubated with or without stimuli at 37° C. for 20 h for induction of Interelukin 6. Interleukin 6 levels in culture supernatants are quantitated by ELISA. Representative MIF inhibitors were tested in the assay described above, specifically, human peripheral blood mononuclear cells [PBMCs] were isolated and stimulated with either LPS or rhMIF. Representative MIF inhibitors were preincubated at a final concentration of 25 µM for 1 hour prior to stimulation and inhibition of TNF-α and IL-6 production was determined at 24 hours. The results are tabulated in Tables 2a, 2b, and 2c below wherein "E" represents ≤10% inhibition; "F" represents >10% inhibition and ≤50% inhibition; and "G" represents >50% inhibition and ≤70% inhibition; and "H" represents >70% inhibition.

TABLE 2a

TNF-α % Inhibition [LPS-stimulated PBMCs]

| Compound | % Inhibition |
|---|---|
| XXI | E |
| IV | F |
| XXVIII | F |
| VIII | F |
| XXXIII | G |
| XXIV | G |
| XVII-1 | G |
| V | H |

TABLE 2b

TNF-α % Inhibition [rhMIF-stimulated PBMCs]

| Compound | % Inhibition |
|---|---|
| XXI | F |
| XXXV | F |
| XXXVI | H |
| XXIV | H |

TABLE 2c

IL-6% Inhibition [rhMIF-stimulated PBMCs]

| Compound | % Inhibition |
|---|---|
| XXIV | F |
| XXI | F |

Example 19

In Vivo Pharmacodynamic Analysis

The ability of candidate compounds to impact cytokine production in vivo will be determined in an acute murine endotoxic shock model. In this model, mice (4-6/group) are injected with low levels of lipopolysaccharide (LPS) to induce cytokine production in a MIF dependent manner. Compounds will be administered either orally or through interperitoneal injection (1-20 mg/kg) using an appropriate vehicle 1 to 24 hours prior to LPS challenge. Serum cytokines (IL-1, TNF-α, IL-6, etc.) will be quantitated from blood drawn 60-240 minutes following challenge by ELISA.

Reference List

Bernhagen, J., Krohn, R., Lue, H., Gregory, J. L., Zernecke, A., Koenen, R. R., Dewor, M., Georgiev, I., Schober, A., Leng, L., Kooistra, T., Fingerle-Rowson, G., Ghezzi, P., Kleemann, R., McColl, S. R., Bucala, R., Hickey, M. J., and Weber, C. (2007). MIF is a noncognate ligand of CXC chemokine receptors in inflammatory and atherogenic cell recruitment. Nat. Med. 13, 587-596.

Calandra, T. and Roger, T. (2003). Macrophage migration inhibitory factor: a regulator of innate immunity. Nat. Rev. Immunol. 3, 791-800.

Cho, Y., Crichlow, G. V., Vermeire, J. J., Leng, L., Du, X., Hodsdon, M. E., Bucala, R., Cappello, M., Gross, M., Gaeta, F., Johnson, K., and Lolis, E. J. (2010). Allosteric inhibition of macrophage migration inhibitory factor revealed by ibudilast. Proc. Natl. Acad. Sci. U.S.A 107, 11313-11318.

Cournia, Z., Leng, L., Gandavadi, S., Du, X., Bucala, R., and Jorgensen, W. L. (2009). Discovery of human macrophage migration inhibitory factor (MIF)-CD74 antagonists via virtual screening. J. Med. Chem. 52, 416-424.

Fingerle-Rowson, G., Kaleswarapu, D. R., Schlander, C., Kabgani, N., Brocks, T., Reinart, N., Busch, R., Schutz, A., Lue, H., Du, X., Liu, A., Xiong, H., Chen, Y., Nemajerova, A., Hallek, M., Bernhagen, J., Leng, L., and Bucala, R. (2009). A tautomerase-null macrophage migration inhibitory factor (MIF) gene knock-in mouse model reveals that protein interactions and not enzymatic activity mediate MIF-dependent growth regulation. Mol. Cell. Biol. 29, 1922-1932.

Gore, Y., Starlets, D., Maharshak, N., Becker-Herman, S., Kaneyuki, U., Leng, L., Bucala, R., and Shachar, I. (2008). Macrophage migration inhibitory factor induces B cell survival by activation of a CD74-CD44 receptor complex. J. Biol. Chem. 283, 2784-2792.

Greven, D., Leng, L., and Bucala, R. (2010). Autoimmune diseases: MIF as a therapeutic target. Expert. Opin. Ther. Targets. 14, 253-264.

McLean, L. R., Zhang, Y., Li, H., Choi, Y. M., Han, Z., Vaz, R. J., and Li, Y. (2010). Fragment screening of inhibitors for MIF tautomerase reveals a cryptic surface binding site. Bioorg. Med. Chem. Lett. 20, 1821-1824.

Morand, E. F., Leech, M., and Bernhagen, J. (2006). MIF: a new cytokine link between rheumatoid arthritis and atherosclerosis. Nat. Rev. Drug Discov. 5, 399-410.

Ouertatani-Sakouhi, H., Liu, M., El-Turk, F., Cuny, G. D., Glicksman, M. A., and Lashuel, H. A. (2010). Kinetic-based high-throughput screening assay to discover novel classes of macrophage migration inhibitory factor inhibitors. J. Biomol. Screen. 15, 347-358.

Schwartz, V., Lue, H., Kraemer, S., Korbiel, J., Krohn, R., Ohl, K., Bucala, R., Weber, C., and Bernhagen, J. (2009). A functional heteromeric MIF receptor formed by CD74 and CXCR4. FEBS Lett. 583, 2749-2757.

Weber, C., Kraemer, S., Drechsler, M., Lue, H., Koenen, R. R., Kapurniotu, A., Zernecke, A., and Bernhagen, J. (2008). Structural determinants of MIF functions in CXCR2-mediated inflammatory and atherogenic leukocyte recruitment. Proc. Natl. Acad. Sci. U.S.A 105, 16278-16283.

Equivalents

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of the Formula III:

III

[Chemical structure of Formula III showing a pyridinone core with substituents $X_5$, $X_6$, $X_7$, $X_8$, $R_5$, $R_6$, linker L, W, W', $Y_1$, $Z_1$, and $R_1$]

or a pharmaceutically acceptable salt, hydrate, solvate or tautomer thereof;

wherein:

each of $X_5$, $X_6$, $X_7$, and $X_8$ is independently CH;

$R_5$ is —$C_1$-$C_6$ alkyl, —$C_2$-$C_6$ alkene, —($C_0$-$C_3$ alkyl)—($C_3$-$C_6$ cycloalkyl), —C(O)$C_1$-$C_6$alkyl, —C(O)NH($C_1$-$C_6$ alkyl), or benzyl, and wherein $R_5$ is optionally substituted;

$R_6$ is —CN;

L is a bond or —$NR_2$—;

each n and p is 1;

each W and W' is independently N or CH, provided that when L is a bond and p and n are each 2 then W and W' cannot simultaneously both be N;

$Y_1$ is null, a bond, —C(O)—, $NR_2$—, $SO_2$, S(O), or O;

$Z_1$ is O, S, —C(O)—, —C(O)N($R_3$)($R_4$), —N($R_3$)($R_4$), —$SO_2$—, or —$SO_2$N($R_3$)($R_4$);

$R_1$ is null, an aromatic monocyclic carbocyle or an aromatic monocyclic heterocycle, wherein $R_1$ is optionally substituted;

$R_2$ is H; and $R_3$ and $R_4$, when taken together with the nitrogen to which they are attached, can optionally form a heterocycle containing from one to three heteroatoms selected from N, O, and S, and wherein $R_3$ and $R_4$ are optionally substituted.

2. The compound of claim 1, wherein $R_1$ is selected from the group consisting of

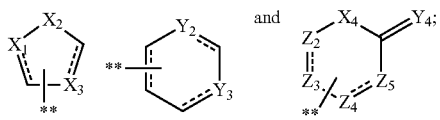

wherein
- each ------ represents a double bond;
- each of $X_1$ and $X_3$ is independently CH, O, S, or $NR_2$, provided that when $X_1$ or $X_3$ are attached to a single bond, then each of $X_1$ and $X_3$ is independently $CH_2$, O, S, or $NR_2$;
- $X_2$ is $CH_2$, O, S, or $NR_2$;
- $X_4$ is $NR_2$, $CH_2$, or O;
- each of $Y_2$ and $Y_3$ is CH or N; provided that when $Y_2$ or $Y_3$ are attached to a single bond, then each of $Y_2$ and $Y_3$ is independently $CH_2$, or $NR_2$;
- $Y_4$ is O or S; and
- each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently $CH_2$, or $NR_2$.

3. The compound of claim 1, wherein $R_1$ is

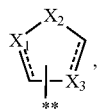

$X_1$ and $X_3$ are each CH; and
each ------ represents a double bond.

4. The compound of claim 1, wherein W is CH and W' is N.

5. The compound of claim 1, wherein $Y_1$ is a bond and $Z_1$ is —C(O)—.

6. The compound of claim 1, wherein $R_5$ is benzyl.

7. A compound having the Formula IIIf:

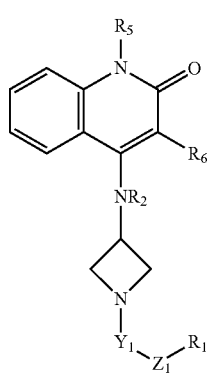

IIIf or a pharmaceutically acceptable salt, hydrate, solvate or tautomer thereof;

wherein
- $Y_1$ is a bond, —C(O)—, —$CH_2$—, or O;
- $Z_1$ is —C(O)—, —C(O)N($R_3$)($R_4$), —N($R_3$)($R_4$), —$SO_2$—, or —$SO_2$N($R_3$)($R_4$);
- $R_1$ selected from the group consisting of null,

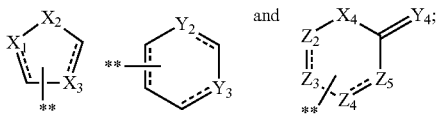

wherein
- each ------ represents a double bond;
- each of $X_1$ and $X_3$ is independently CH, O, S, or $NR_2$, provided that when $X_1$ or $X_3$ are attached to a single bond, then each of $X_1$ and $X_3$ is independently $CH_2$, O, S, or $NR_2$;
- $X_2$ is $CH_2$, O, S, or $NR_2$;
- $X_4$ is $NR_2$, $CH_2$, or O;
- each of $Y_2$ and $Y_3$ is CH or N; provided that when $Y_2$ or $Y_3$ are attached to a single bond, then each of $Y_2$ and $Y_3$ is independently $CH_2$, or $NR_2$;
- $Y_4$ is O or S;
- each of $Z_2$, $Z_3$, $Z_4$, and $Z_5$ is independently N or CH; provided that when $Z_2$, $Z_3$, $Z_4$, and $Z_5$ are attached to a single bond, then each of $Z_2$, $Z_3$, $Z_4$, and $Z_5$ is independently $CH_2$, or $NR_2$; and
- $R_1$ is optionally substituted;
- $R_2$ is H;
- $R_3$ and $R_4$, when taken together with the nitrogen to which they are attached, can optionally form a heterocycle containing from one to three heteroatoms selected from N, O, and S, and wherein $R_3$ and $R_4$ are optionally substituted; and
- $R_6$ is —CN.

8. The compound of claim 7, wherein $R_1$ is

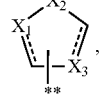

$X_1$ and $X_3$ are each CH; and
each ------ represents a double bond.

9. The compound of claim 7, wherein $R_1$ is

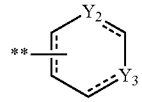

and $Y_3$ is CH and
each ------ represents a double bond.

10. The compound of claim 1, selected from the group consisting of:
- 1-methyl-2-oxo-4-(1-(thiophene-2-carbonyl)azetidin-3-ylamino)-1,2-dihydroquinoline-3-carbonitrile;
- 1-methyl-4-(1-(methylsulfonyl)azetidin-3-ylamino)-2-oxo-1,2-dihydroquinoline-3-carbonitrile;
- 1-(4-fluorobenzyl)-2-oxo-4-(1-(thiophen-2-ylsulfonyl)azetidin-3-ylamino)-1,2-dihydroquinoline-3-carbonitrile; and
- 1-(4-fluorobenzyl)-4-(1-isonicotinoylazetidin-3-ylamino)-2-oxo-1,2-dihydroquinoline-3-carbonitrile.

11. A pharmaceutical formulation, comprising a therapeutically effective amount of a compound according to claim 1 and a pharmaceutically acceptable carrier.

12. A pharmaceutical formulation, comprising a therapeutically effective amount of a compound according to claim 7 and a pharmaceutically acceptable carrier.

* * * * *